US008918175B2

(12) United States Patent
Nelson et al.

(10) Patent No.: US 8,918,175 B2
(45) Date of Patent: Dec. 23, 2014

(54) ELECTRICAL STIMULATION THERAPY FOR LOWER URINARY TRACT DYSFUNCTION AND SEXUAL REFLEX DYSFUNCTION

(71) Applicant: Medtronic, Inc., Minneapolis, MN (US)

(72) Inventors: Dwight E. Nelson, Shoreview, MN (US); Xin Su, Shoreview, MN (US); Thaddeus S. Brink, St. Paul, MN (US); Blake A. Hedstrom, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/778,348

(22) Filed: Feb. 27, 2013

(65) Prior Publication Data

US 2013/0289659 A1    Oct. 31, 2013

Related U.S. Application Data

(60) Provisional application No. 61/636,970, filed on Apr. 23, 2012.

(51) Int. Cl.
| | | |
|---|---|---|
| *A61N 1/05* | (2006.01) | |
| *A61N 1/08* | (2006.01) | |
| *A61N 1/36* | (2006.01) | |
| *A61B 5/021* | (2006.01) | |
| *A61B 5/00* | (2006.01) | |
| *A61B 5/024* | (2006.01) | |

(52) U.S. Cl.
CPC . *A61N 1/08* (2013.01); *A61B 5/021* (2013.01); *A61B 5/4393* (2013.01); *A61B 5/4255* (2013.01); *A61N 1/36007* (2013.01); *A61N 1/36171* (2013.01); *A61N 1/3615* (2013.01); *A61B 5/024* (2013.01); *A61N 1/36107* (2013.01); *A61B 5/4368* (2013.01)
USPC .......................................................... 607/41

(58) Field of Classification Search
None
See application file for complete search history.

(56) References Cited

U.S. PATENT DOCUMENTS

| | | | |
|---|---|---|---|
| 7,047,078 B2 | 5/2006 | Boggs, II et al. | |
| 7,369,894 B2 | 5/2008 | Gerber | |
| 7,623,925 B2 | 11/2009 | Grill et al. | |
| 7,809,443 B2 | 10/2010 | Giftakis et al. | |
| 2007/0100387 A1* | 5/2007 | Gerber | 607/41 |
| 2008/0183236 A1 | 7/2008 | Gerber | |
| 2009/0036945 A1 | 2/2009 | Chancellor et al. | |

* cited by examiner

*Primary Examiner* — Brian T Gedeon
*Assistant Examiner* — Ankit Tejani
(74) *Attorney, Agent, or Firm* — Shumaker & Sieffert, P.A.

(57) ABSTRACT

Electrical stimulation therapy may be delivered to a patient to selectively and independently address different conditions of a pelvic floor disorder of the patient. The conditions of a pelvic floor disorder may include, for example, a lower urinary tract dysfunction (e.g., urinary or fecal incontinence) and sexual dysfunction (e.g., an impaired sexual reflex response to a sexual stimulus). In some examples, a system is configured to selectively deliver a first electrical stimulation therapy that is configured to elicit an inhibitory physiological response from the patient related to voiding, a second electrical stimulation therapy that is configured to improve a sexual reflex response of the patient to a sexual stimulus, and a third electrical stimulation therapy that is configured to both elicit the inhibitory physiological response from the patient related to voiding and increase a sexual response of the patient to a sexual stimulus.

20 Claims, 15 Drawing Sheets

FIG. 8A
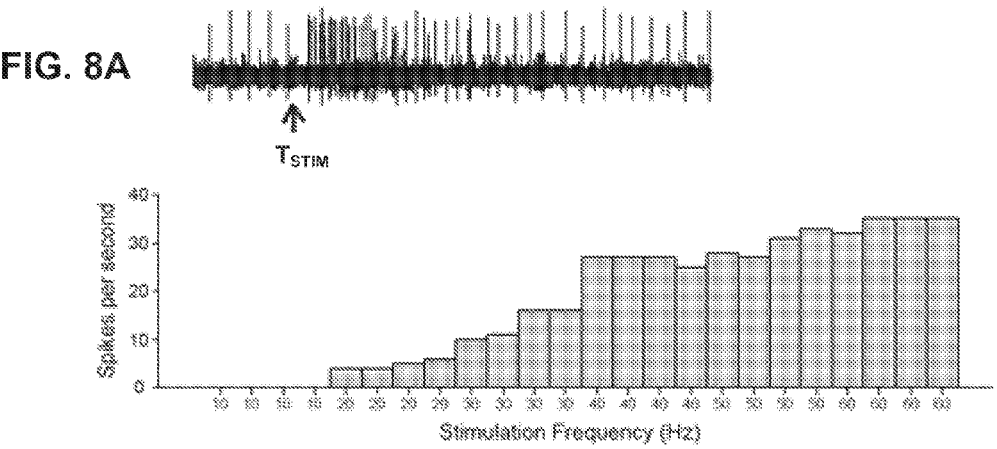
FIG. 8B
FIG. 9A
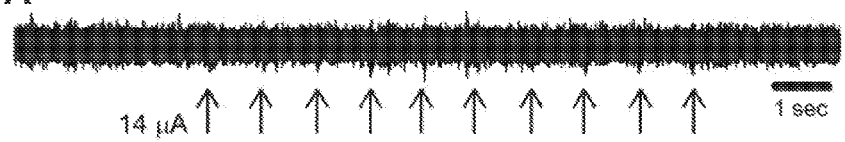
FIG. 9B
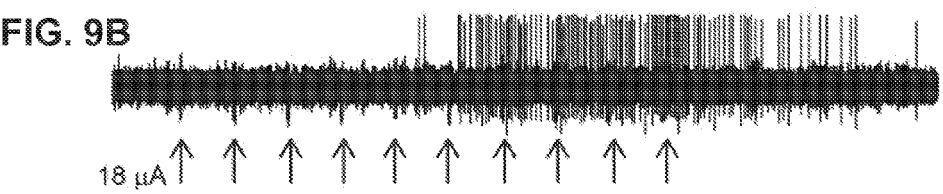
FIG. 9C
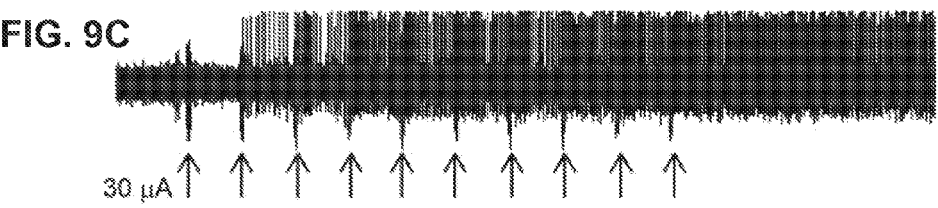

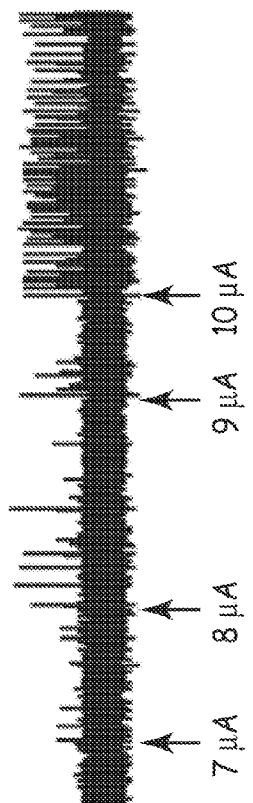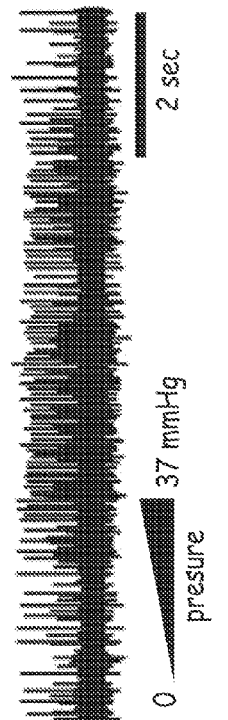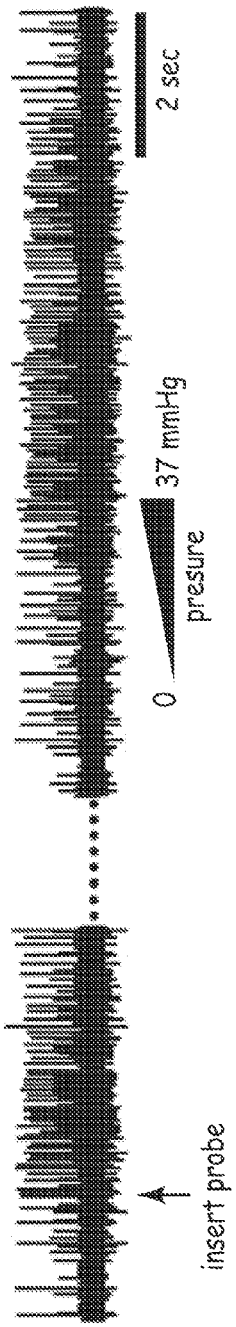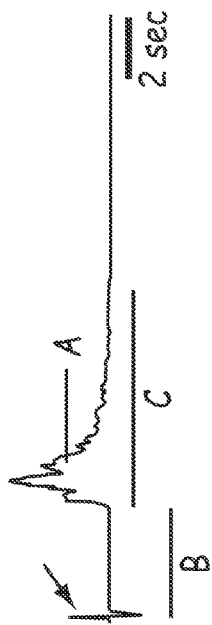
FIG. 11A
FIG. 11B
FIG. 11C
FIG. 12A
FIG. 12B

ELECTRICAL STIMULATION THERAPY FOR LOWER URINARY TRACT DYSFUNCTION AND SEXUAL REFLEX DYSFUNCTION

TECHNICAL FIELD

The disclosure relates to medical devices and, more particularly, medical devices for treatment of a pelvic floor disorder.

BACKGROUND

Electrical stimulation therapy has been proposed to treat a variety of patient symptoms or conditions, such as pelvic floor disorders of patients. Pelvic floor disorders may include urinary incontinence (e.g., stress incontinence or urge incontinence), fecal incontinence, pelvic pain, bowel dysfunction, and sexual dysfunction. Some electrical stimulation systems include one or more electrodes coupled to an IMD via one or more leads, while other electrical stimulation systems include leadless stimulators.

SUMMARY

In general, the disclosure is directed to devices and systems configured to deliver electrical stimulation therapy to a patient to selectively and independently address different conditions of a pelvic floor disorder of the patient, and methods for delivering the electrical stimulation therapy. The conditions of a pelvic floor disorder may include, for example, a lower urinary tract dysfunction (e.g., urinary or fecal incontinence) and sexual dysfunction (e.g., an impaired sexual reflex response to a sexual stimulus).

In some examples, a system is configured to selectively deliver a first electrical stimulation therapy that is configured to elicit an inhibitory physiological response from the patient related to voiding (e.g., reduce a bladder contraction frequency of the patient), a second electrical stimulation therapy that is configured to improve a sexual reflex response (e.g., shorten a response period) of the patient to a sexual stimulus, and a third electrical stimulation therapy that is configured to both elicit an inhibitory physiological response from the patient related to voiding of the patient and increase a sexual response of the patient to a sexual stimulus. In this example, the first and third electrical stimulation therapies are configured to elicit a greater inhibitory physiological response from the patient related to voiding (e.g., a greater reduction in bladder contraction frequency) compared to the second electrical stimulation therapy, and the second and third electrical stimulation therapies are configured to elicit a greater increase a sexual reflex response of the patient to a sexual stimulus compared to the first electrical stimulation therapy. In some examples, the electrical stimulation parameter values of the first electrical stimulation therapy may be selected to elicit an inhibitory physiological response from the patient related to voiding with no impact on sexual function, e.g., without any genital sensations.

In some examples, a system is configured to select one of the first, second or third electrical stimulation therapies in response to user input (e.g., patient input) and deliver electrical stimulation therapy to the patient in accordance with the selected electrical stimulation therapy. The user input may, for example, be associated with a particular physiological response from the patient that is associated with one of the first, second, or third electrical stimulation therapies. In this way, the system may be configured to deliver electrical stimulation therapy that selectively elicits a particular physiological response from the patient when user input associated with the particular physiological response is received. In some examples, a medical device may deliver one of the stimulation therapies as a part of chronic therapy delivery, and, in response to receiving user input selecting one of the other two electrical stimulation therapies, select the other electrical stimulation therapy and deliver electrical stimulation therapy to the patient in accordance with the selected electrical stimulation therapy.

In one example, the disclosure is directed to a method comprising, with a processor, receiving user input, with the processor, selecting, based on the user input, one of a first electrical stimulation therapy configured to elicit an inhibitory physiological response from the patient related to voiding, a second electrical stimulation therapy configured to increase a sexual response of the patient to a sexual stimulus compared to a physiological state of the patient elicited by the first electrical stimulation therapy, or a third electrical stimulation therapy configured to elicit the inhibitory physiological response from the patient related to voiding and, compared to the physiological state of the patient elicited by the first electrical stimulation therapy, and, with the processor, controlling a medical device to deliver the selected one of the first electrical stimulation therapy, the second electrical stimulation therapy or the third electrical stimulation therapy to the patient.

In another example, the disclosure is directed to a system comprising a medical device, and a processor configured to receive input from a user, and select, based on the user input, one of a first electrical stimulation therapy configured to elicit an inhibitory physiological response from the patient related to voiding, a second electrical stimulation therapy configured to increase a sexual response of the patient to a sexual stimulus compared to a physiological state of the patient elicited by the first electrical stimulation therapy, or a third electrical stimulation therapy configured to elicit the inhibitory physiological response from the patient related to voiding and, compared to the physiological state of the patient elicited by the first electrical stimulation therapy, increase the sexual response of the patient to the sexual stimulus, wherein the processor is configured to control the medical device to deliver the selected one of the first electrical stimulation therapy, the second electrical stimulation therapy or the third electrical stimulation therapy to the patient.

In another example, the disclosure is directed to a system comprising means for receiving user input, and means for selecting, based on the user input, one of a first electrical stimulation therapy configured to elicit an inhibitory physiological response from the patient related to voiding, a second electrical stimulation therapy configured to increase a sexual response of the patient to a sexual stimulus compared to a physiological state of the patient elicited by the first electrical stimulation therapy, or a third electrical stimulation therapy configured to elicit the inhibitory physiological response from the patient related to voiding, and, compared to the physiological state of the patient elicited by the first electrical stimulation therapy, increase the sexual response of the patient to the sexual stimulus. The system further comprises means for controlling a medical device to deliver the selected one of the first electrical stimulation therapy, the second electrical stimulation therapy or the third electrical stimulation therapy to the patient.

In another example, the disclosure is directed to a computer-readable medium comprising instructions. When executed by a processor, the instructions cause a processor to receive user input and select, based on the user input, one of a first electrical stimulation therapy configured to reduce a bladder contraction frequency of the patient, a second electrical stimulation therapy configured to increase a sexual response of the patient to a sexual stimulus compared to a physiological state of the patient elicited by the first electrical stimulation therapy, or a third electrical stimulation therapy configured to reduce the bladder contraction frequency of the patient and increase the sexual response of the patient to the sexual stimulus compared to the physiological state of the patient elicited by the first electrical stimulation therapy. The instructions may further cause the processor to control a medical device to deliver the selected one of the first electrical stimulation therapy, the second electrical stimulation therapy or the third electrical stimulation therapy to the patient.

In another aspect, the disclosure is directed to a computer-readable storage medium, which may be a non-transitory article of manufacture. The computer-readable storage medium includes computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein.

The details of one or more examples are set forth in the accompanying drawings and the description below. Other features, objects, and advantages will be apparent from the description and drawings, and from the claims.

BRIEF DESCRIPTION OF DRAWINGS

FIG. 8A is a graph that illustrates an example excitatory response of a test subject to a plurality of different stimulation signal frequencies (from 10 Hertz (Hz) to 90 Hz).

FIG. 8B illustrates a frequency-response profile for an individual medullary reticular formation (MRF) neuron of a test subject.

FIGS. 9A-9C are graphs that illustrate the response of an MRF neuron of a test subject to bilateral dorsal nerve of the penis neuromodulation and illustrate the dependence of the excitatory response of the MRF neuron on the intensity of electrical stimulation delivered to the target site.

FIGS. 11A-11C are individual recordings of a single MRF neuron of a subject and illustrate responses of the individual MRF neuron of a test subject to several stimuli.

FIG. 12A illustrates an example compound action potential indicative of a pudendal motor reflex discharge response to electrical stimulation of the right dorsal nerve of the penis of a test subject, and FIG. 12B illustrates an example compound action potential indicative of a control pudendal motor reflex discharge response of the test subject.

DETAILED DESCRIPTION

Figure 1:
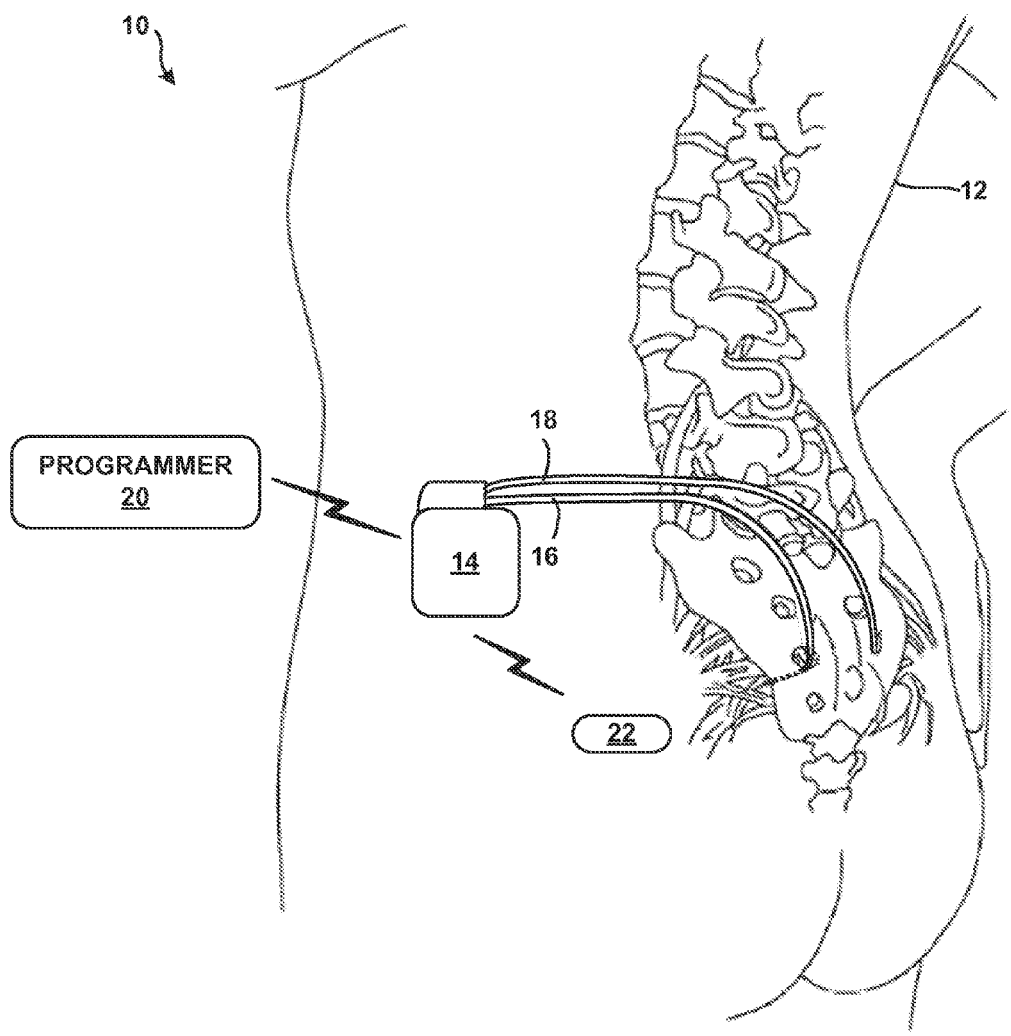
FIG. 1 is a conceptual diagram of an example therapy system that selectively delivers a first electrical stimulation therapy that is configured to reduce a bladder contraction frequency of a patient, a second electrical stimulation therapy that is configured to improve a sexual reflex response of the patient to a sexual stimulus, and a third electrical stimulation therapy is configured to both reduce a bladder contraction frequency of the patient and increase a sexual response of the patient to a sexual stimulus.

Some patient disorders may cause or otherwise be associated with dysfunctions of the lower urinary tract and sexual reflex. The dysfunctions of the lower urinary tract and sexual reflex may coexist in some patients and may be due to altered sensitivity, irritation from pelvic organs, such as the urinary bladder or pelvic floor muscle, or both. Example dysfunctions of the lower urinary tract include improper functioning of the bladder or urinary tract, and may include, for example, an overactive bladder, urgency, urine retention disorder, or urinary incontinence. Urgency is a sudden, compelling urge to urinate, and may, though not always, be associated with urinary incontinence. Urinary incontinence refers to a condition of in which involuntary voiding events may occur (i.e., involuntary loss of urine), and may include urge incontinence, stress incontinence, or both stress and urge incontinence, which may be referred to as mixed urinary incontinence. Symptoms of overactive bladder may include urgency, frequent urination, or both.

One type of therapy that has been proposed for managing lower urinary tract dysfunction (e.g., minimizing bladder contractions and/or the number of involuntary voiding events) includes delivery of electrical stimulation to a target tissue site within a patient. For example, delivery of electrical stimulation from an implantable medical device to a target tissue site proximate any one or more of a spinal nerve, a sacral nerve, a pudendal nerve, dorsal genital nerve (e.g., the dorsal nerve of the penis or clitoris), an inferior rectal nerve, a perineal nerve, a nerve tract of the leg (e.g., sciatic nerve, peroneal nerve or tibial nerve) or branches of any of the aforementioned nerves to modulate the nerve activities may provide an effective therapy for managing lower urinary tract dysfunction. As an example, electrical stimulation to modulate the activity of the sacral nerve, the dorsal-genital nerve, and/or the pudendal nerve (or branches of these nerves) may help reduce bladder contraction frequency, which can mitigate urgency.

A sexual reflex dysfunction may increase the response time of the patient to a sexual stimulus relative to a healthy patient, such that it may take a relatively long time (relative to a healthy patient) for the patient to become sexually aroused. This may be referred to as an impairment of the sexual reflex response of the patient. For example, it may take a patient with a sexual dysfunction longer to reach the first phase of the human sexual response cycle compared to a healthy patient. During the first phase of the human sexual response cycle, the patient may exhibit an increase in heart rate, respiratory rate, blood pressure, or exhibit other changes in physiological parameters indicative of sexual arousal in response to a sexual stimulus.

A number of spinally-mediated reflexes may be involved in providing a sexual reflex response (including sexual arousal) to a sexual stimulus. Example spinally-mediated reflexes include sensation and motor outputs (e.g., the pudendal motor reflex discharge of the motor component of the pudendal nerve) related to sexual function. A patient disorder may affect a neural network associated with these spinally-mediated reflexes, and, as a result, the sexual response reflex of the patient may be impaired (e.g., the response time for reaching the first phase of the human sexual response cycle may increase relative to a healthy patient without such an impairment). A neural network is a circuit of biological neurons that are connected or functionally related, such that modulation of one part of the network may affect the activity of neurons in other parts of the network.

The medullary reticular formation (MRF) neurons in a brain of a patient form part of the neural network that is associated with sexual function. Delivery of electrical stimulation to modulate one or more neural networks associated with sexual function may lead to improvements in sexual function, such as a more responsive sexual reflex (e.g., a shorter response time for reaching the first phase of the human sexual response cycle relative to a baseline state in which no therapy is delivered to the patient with the impaired sexual reflex response). For example, as discussed in further detail below, electrical stimulation therapy delivered to modulate activity of the dorsal genital nerve may alter the firing of MRF neurons in the brain of the patient, which have been shown to have a specific link to the sexual arousal of a subject in response to a sexual stimulus. In addition, as discussed in further detail below with respect to FIGS. 8A-17, the delivery of electrical stimulation to modulate activity of the dorsal genital nerve, i.e., neuromodulation of the dorsal genital nerve, has been shown to change pudendal motor nerve activity, including the pudendal motor reflex discharge.

The pudendal motor reflex discharge is a compound action potential of the pudendal nerve that is involved in certain somatic sexual reflexes. Changes in the pudendal motor reflex discharge response of a patient may indicate changes in the sexual reflex response of a patient to a sexual stimulus because the motor output of a patient may increase in response to a sexual stimulus. Thus, the latency, duration, and magnitude of the pudendal motor reflex discharge response may indicate the relative level of the sexual reflex response of the patient.

Some neural networks associated with the sensation and motor outputs related to sexual function are located in some of the same structures as neural networks associated with dysfunctions of the lower urinary tract. For example, as discussed in further detail below, electrical stimulation delivered to a modulate activity of a dorsal genital nerve of the patient may provide efficacious therapy for lower urinary tract dysfunction and sexual dysfunction.

The dorsal genital nerve is a sensory nerve innervating the sexual organs and urethra. The dorsal genital nerve merges with several nerves, including the inferior rectal nerve and the perineal nerve, at which point the nerves become the compound pudendal nerve. As the pudendal nerve approaches the spinal cord, it joins with other nerves, including the pelvic nerve, at the sacral plexus before becoming distinct sacral roots (e.g., S1-S4/5), which enter into the spinal cord. As discussed in further detail below with respect to FIGS. 8A-17, experimental results demonstrate that neuromodulation of any one or more of the dorsal genital nerve, compound pudendal nerve, or L6 spinal nerve may alter both urinary physiology, as well as sexual function physiology.

It is believed that electrical stimulation parameters for modulating sexual function (e.g., improving the sexual reflex response of the patient) may be distinct from those used in the modulation of urinary and excretory functions. Accordingly, electrical stimulation parameters, such as a frequency or intensity (which may be a function of one or more parameters, such as current of voltage pulse amplitude, pulse rate, and pulse width), can be used to modulate urinary tract control systems separately from sexual neural networks of the patient, even when electrical stimulation is delivered to the same target nerve. In this way, devices and systems may be configured to deliver electrical stimulation therapy to a patient to selectively and independently address different conditions of a pelvic floor disorder of the patient, such as lower urinary tract dysfunction and sexual reflex response dysfunction. The therapy delivery techniques described herein that selectively and independently address different conditions of a pelvic floor disorder of the patient may improve sensory differentiation.

FIG. 1 is a conceptual diagram that illustrates an example of a therapy system 10 that is configured to deliver electrical stimulation therapy to patient 12 to manage a lower urinary tract dysfunction of patient 12 and sexual reflex response dysfunction of patient 12. As described in further detail below, in some examples, therapy system 10 is configured to selectively deliver a first electrical stimulation therapy that is configured to elicit an inhibitory physiological response from patient 12 related to voiding (e.g., reduce a bladder contraction frequency, urgency, or urge incontinence of patient 12), a second electrical stimulation therapy that is configured to improve a sexual reflex response of patient 12 to a sexual stimulus, and a third electrical stimulation therapy is configured to both elicit an inhibitory physiological response from patient 12 related to voiding and increase a sexual response of patient 12 to a sexual stimulus. The first and third electrical stimulation therapies are configured to elicit a greater inhibitory physiological response from patient 12 related to voiding (e.g., a greater reduction in bladder contraction frequency) compared to the second electrical stimulation therapy, and the second and third electrical stimulation therapies are configured to elicit a greater increase in a sexual reflex response of patient 12 to a sexual stimulus compared to the physiological state of patient 12 elicited by the first electrical stimulation therapy.

In some examples, the first electrical stimulation therapy may have some incidental impact on the sexual function of patient 12, but the impact is less than that elicited by the second and third stimulation therapies. In other examples, the first electrical stimulation therapy may be configured (e.g., based on the electrical stimulation parameter values that define the first electrical stimulation therapy) to elicit an inhibitory physiological response from patient 12 related to voiding, and have no impact on sexual function of patient 12. For example, as discussed in further detail below, it is believed that the lower frequency electrical stimulation (e.g., less than about 10 Hz) may have little to no impact on sexual function of patient 12.

Similarly, the second electrical stimulation therapy may elicit some inhibitory physiological response from patient 12 related to voiding in some examples. However, this response is believed to be less inhibitory than that elicited by the first and third stimulation therapies, e.g., due to the higher frequency stimulation of the second electrical stimulation therapy compared to the first stimulation therapy.

Therapy system 10 includes an implantable medical device (IMD) 14, which is coupled to leads 16, 18. System 10 also includes an external programmer 20, which is configured to communicate with IMD 14 via a wireless communication protocol. In some examples, system 10 may include sensor 22, which is configured to generate a signal indicative of a patient parameter of patient 12. The patient parameter may be, for example, indicative of a condition of patient 12 related to lower urinary tract dysfunction, e.g., relating to a bladder fill level, bladder contraction or a posture or activity level of patient 12, or sexual reflex response, e.g., a heart rate, respiratory rate, blood pressure, and the like. As shown in FIG. 1, sensor 22 and IMD 14 may be configured to communicate with each other via a wireless communication protocol. For example, sensor 22 may be configured to transmit a signal indicative of a sensed physiological parameter of patient 12 to IMD 14. IMD 14 is configured to operate as a therapy device that delivers electrical stimulation therapy to patient 12 by generating and delivering a programmable electrical stimulation signal (e.g., in the form of electrical pulses or a continuous waveform) to target therapy sites proximate electrodes of leads 16, 18. In the example shown in FIG. 1, the electrodes of each lead 16, 18 are disposed proximate to a distal end of the respective lead 16, 18. The target tissue sites can be, for example, proximate a spinal nerve, a sacral nerve, a pudendal nerve, dorsal genital nerve, a tibial nerve, an inferior rectal nerve, a perineal nerve, or branches of any of the aforementioned nerves. The target tissue sites may be selected based on the type of dysfunctions for which therapy system 10 is implemented to treat. For example, in the example shown in FIG. 1, the target tissue sites may be selected such that delivery of electrical stimulation to the tissue sites may selectively modulate the neural networks for lower urinary tract dysfunction and sexual reflex response dysfunction of patient 12. An example of such a tissue site is the dorsal genital nerve.

In some examples, the target tissue sites can be identified prior to implantation of leads 16, 18. For example, a device, such as an introducer or needle, can be introduced into patient 12 and a test electrical signal can be delivered to tissue of patient 12 via the device. The device may be moved within patient 12 until a desirable physiological response is elicited by the test electrical signal, which can indicate that the device (e.g., the one or more electrodes used to deliver the test stimulation) is positioned at a tissue site that captures a target nerve. In some examples, the physiological response may be detected through a motor response that may be visually detected, a sensory response as reported by the patient, or through an electrical response (e.g., sensed nerve signals). Electrodes of leads 16, 18 can subsequently be positioned at the tissue site at which the test electrical signal elicited the desirable physiological response. In other examples, the test stimulation may be delivered via leads 16, 18.

In some examples, IMD 14 may be surgically implanted in patient 12 at any suitable location within patient 12, such as in the side of the lower abdomen or the side of the lower back or upper buttocks. IMD 14 can include a biocompatible outer housing, which may be formed from titanium, stainless steel, a liquid crystal polymer, or the like. One or more medical leads, e.g., leads 16, 18, may be connected to IMD 14 and surgically or percutaneously tunneled to place one or more electrodes of the respective lead at a target tissue site proximate to a desired nerve or muscle, e.g., one of the previously listed target therapy sites, such as a tissue site proximate a spinal, sacral or pudendal nerve. The proximal ends of leads 16, 18 are both electrically and mechanically coupled to IMD 14 either directly or indirectly, e.g., via respective lead extensions.

Electrical conductors disposed within the lead bodies of leads 16, 18 electrically connect electrodes of the respective lead to a therapy delivery module (e.g., a stimulation generator) of IMD 14. In addition, in some examples, the electrical conductors of leads 16, 18 electrically connect the electrodes of the respective lead to a sensing module of IMD 14, which enables IMD 14 to sense a physiological parameter of patient 12 via the electrodes.

Leads 16, 18 can be positioned to deliver stimulation to target tissue sites proximate branches of the same nerve or branches of different nerves. For example, IMD 14 can deliver bilateral stimulation to patient 12 by delivering stimulation to both the left and right nerve branches (or portions) of the same nerve and/or by delivering stimulation to a left branch of a first nerve and a right branch of a second nerve that is different than the first nerve. As an example, leads 16, 18 can be positioned to deliver electrical stimulation to tissue sites on both lateral sides of patient 12 to modulate activity of both a left and a right dorsal genital nerve or nerve portion, both a left and a right pudendal nerve or nerve portion, and/or both a dorsal genital nerve or nerve portion and a pudendal nerve or nerve portion on different lateral sides of patient 12.

Data from experiments discussed below with respect to FIGS. 8A-17 demonstrates that electrical stimulation at similar or different amplitudes, but higher frequencies (e.g., greater than about 18 Hz, such as about 18.1 Hz to about 40 Hz, or greater than about 40.1 Hz, such as about 50 Hz or about 80 Hz) may activate neural networks related to sexual activity and improve a sexual reflex response of patient 12 to a sexual stimulation. Electrical stimulation frequencies in a lower frequency range (e.g., less or equal to about 18 Hz, such as in a range of about 0.1 Hz to about 18 Hz, or about 5 Hz to less than about 14 Hz) may have inhibitory physiological effects on the urinary bladder activity, e.g., may reduce a bladder contraction frequency, urgency, or urge incontinence of patient 12. In addition, electrical stimulation frequency equal to or between about 18.1 Hz and about 40 Hz may both improve a sexual reflex response of patient 12 to a sexual stimulus and have quieting effects on the urinary bladder activity. Thus, by adjusting electrical stimulation parameter values (e.g., frequency levels), IMD 14 may selectively deliver a first electrical stimulation therapy to patient 12 that elicits an inhibitory physiological response related to voiding from patient 12, a second electrical stimulation therapy that activates neural networks if patient 12 related to sexual activity, or a third electrical stimulation therapy that both inhibitory physiological response related to voiding from patient 12 and activates neural networks if patient 12 related to sexual activity.

IMD 14 is configured to deliver, at different times, first and third electrical stimulation therapies, which are each configured to elicit an inhibitory physiological response from patient 12 related to voiding, such as a reduction in bladder contraction frequency of patient 12, which may help address symptoms, such as urinary incontinence, of a lower urinary tract dysfunction of patient 12. Thus, the first and third stimulation therapies are configured to elicit similar inhibitory physiological responses from patient 12 related to voiding. While the second stimulation therapy, which is configured to improve a sexual reflex response of the patient relative to a baseline state in which no therapy, or at least no electrical stimulation therapy, may incidentally elicit an inhibitory physiological response from patient 12 related to voiding, the relative strength of the inhibitory physiological response related to voiding elicited by the second stimulation therapy may be less than the first and third stimulation therapies.

For example, in examples in which the inhibitory physiological response includes a reduction in bladder contraction frequency, the reduction in bladder contraction frequency resulting from the delivery of the first or third stimulation therapies may be greater that the reduction in bladder contraction frequency resulting from delivery of the second stimulation therapy. In this way, any incidental inhibitory physiological response elicited by the delivery of the first or third stimulation therapies may be greater (or stronger) than an inhibitory physiological response elicited by the delivery of the second stimulation therapy.

In addition, IMD 14 is configured to deliver, at different times, second and third electrical stimulation therapies, which are each configured to improve a sexual reflex response of patient 12 to a sexual stimulus, which may help address symptoms of a sexual reflex dysfunction of patient 12. While the first stimulation therapy, which is configured elicit an inhibitory physiological response from patient 12 related to voiding, may incidentally improve a sexual reflex response of patient 12 to a sexual stimulus, the second stimulation therapy and third electrical stimulation therapies may elicit a better improvement in the sexual reflex response of patient 12 to a sexual stimulus. For example, the time for patient 12 to reach the first phase of human sexual activity in response to a sexual stimulus may be shorter when the second stimulation therapy is being delivered to the patient than when the first stimulation therapy.

The second and third electrical stimulation therapy configured to elicit a physiological state of patient 12 in which the sexual reflex response of patient 12 is improved may differ from electrical stimulation therapy used to induce specific phases of sexual activity. The electrical stimulation therapy configured to improve the sexual reflex response of patient 12 may merely prime patient 12 for sexual activity, such that patient 12 is more predisposed to sexual function, rather than elicit specific functional sexual responses (e.g., ejaculation or orgasm) from patient 12.

IMD 14 is configured to selectively deliver one of the first, second or third electrical stimulation therapies to patient 12. Various triggers may be used to initiate the delivery of each of the first, second or third electrical stimulation therapies to patient 12. In some examples, IMD 14 is configured to select at least one of the second or third electrical stimulation therapies in response to user input (e.g., patient input) and deliver electrical stimulation therapy to the patient in accordance with the selected electrical stimulation therapy. The user input may, for example, be associated with a particular physiological response from the patient that is associated with a particular stimulation therapy. In this way, IMD 14 may be configured to deliver electrical stimulation therapy that selectively elicits a particular physiological response from patient 12 when a user input associated with the particular physiological response is received. In other examples, the user input may be associated with a particular therapy program that is associated with a respective one of the first, second or third stimulation therapies.

In these examples, IMD 14 may be configured to deliver the first electrical stimulation therapy to patient 12 as a part of chronic therapy delivery, in response to user input (in a manner similar to that described above with respect to the second and third stimulation therapies), or both. For example, IMD 14 may deliver electrical stimulation therapy to patient 12 in accordance with the first electrical stimulation therapy (and not the second and third electrical stimulation therapies), and, in response to receiving user input select one of the second or third electrical stimulation therapies, IMD 14 may select the electrical stimulation therapy indicated by the user input and deliver electrical stimulation therapy to the patient in accordance with the selected second or third electrical stimulation therapy. IMD 14 may then cease delivering the selected second or third electrical stimulation therapy after some predetermined amount of time, in response to a sensed condition, or in response to user input selecting the first electrical stimulation therapy. At that time, IMD 14 may then revert back to delivering the first electrical stimulation therapy to patient 12.

IMD 14 may deliver the first stimulation therapy in an open loop manner in some examples, in which IMD 14 delivers the first stimulation therapy without intervention from a user or a sensor. In other examples, IMD 14 may deliver the first stimulation therapy in a closed-loop manner. For example, IMD 14 may be configured to deliver the first stimulation therapy for the first time period, and cease delivery of the first stimulation therapy until a trigger event is detected. A trigger event can include, for example, detection of a patient parameter (e.g., a physiological condition) indicative of an increased possibility of an involuntary voiding event or an imminent involuntary voiding event, input from the patient (or a patient caretaker) that indicates that additional therapy to help prevent the occurrence of involuntary voiding event is desirable, or expiration of a timer comprising a predetermined duration of time.

In examples in which the trigger event comprises a physiological condition of patient 12, IMD 14 may detect the physiological condition based on a physiological parameter of patient 12 sensed by, e.g., via sensor 22 or a sensing module of IMD 14. An example of a trigger event comprising a physiological condition is a bladder volume (e.g., as indicated by an impedance of the bladder of patient 12, pressure sensed at a bladder wall, the output of a strain gauge on the bladder wall, and the like) that is indicative of an increased possibility of an involuntary voiding event. Another example of a trigger event comprising a physiological condition is a bladder contraction intensity or bladder contraction frequency at or above a trigger event threshold.

IMD 14 may detect contractions of bladder and determine the bladder contraction frequency and intensity based on any suitable physiological parameter such as, but not limited to, bladder impedance, bladder pressure, pudendal or sacral afferent nerve signals, an electromyogram (EMG) of a relevant muscle (e.g., a urinary sphincter muscle, bladder wall or detrusor muscle), or any combination thereof. Thus, in some examples, sensor 22 may include, for example, a pressure sensor positioned in patient 12 to detect changes in bladder pressure, electrodes for sensing pudendal or sacral afferent nerve signals, electrodes for sensing urinary sphincter EMG signals (or anal sphincter EMG signals in examples in which therapy system 10 provides therapy to manage fecal urgency or fecal incontinence), or any combination thereof. In examples in which IMD 14 detects bladder contractions or a bladder volume (also referred to herein as a fill level) based on an impedance through the bladder of patient 12, which varies as a function of the contraction of the bladder, IMD 14 can determine the impedance through the bladder using any suitable sensing configuration.

As shown in FIG. 1, in some examples, sensor 22 can be physically separate from IMD 14 and can wirelessly transmit signals to IMD 14. Alternatively, sensor 22 may be carried on one of leads 16, 18 or an additional lead coupled to IMD 14. In some examples, sensor 22 may include one or more electrodes for sensing afferent nerve signals or one or more sense electrodes for generating an EMG of a relevant muscle.

One type of bladder contraction detection algorithm indicates an occurrence of a bladder contraction when a signal generated by sensor 22 (or a sensing module of IMD 14 or another sensing module) exhibits a certain characteristic, which may be a time domain characteristic (e.g., a mean, median, peak or lowest signal amplitude within a particular time period) or a frequency domain characteristic (e.g., an energy level in one or more frequency bands or a ratio of energy levels in different frequency bands). Another bladder contraction detection algorithm indicates the occurrence of a bladder contraction if a sensed signal substantially correlates to a signal template, e.g., in terms of frequency, amplitude and/or spectral energy characteristics. IMD 14 may use known techniques to correlate a sensed signal with a template in order to detect the bladder contraction or detect the bladder contraction based on the frequency domain characteristics of a sensed signal. Other bladder contraction techniques may be used.

In addition to or instead of the previously discussed physiological conditions, the trigger event can be a patient activity level (e.g., an indication of the level of motion or movement of one or more of the patient's limbs or trunk) or patient posture state that is indicative of an increased probability of an occurrence of an involuntary voiding event. Sensor 22 may comprise, for example, a patient motion sensor, such as a two-axis accelerometer, three-axis accelerometer, one or more gyroscopes, pressure transducers, piezoelectric crystals, or other sensor that generates a signal that changes as patient activity level or posture state changes. In some examples, IMD 14 initiates the delivery of the first stimulation therapy to patient 12 upon detecting a patient activity level exceeding a particular threshold based on the signal from the motion sensor. The patient activity level that is greater than or equal to a trigger event threshold (which may be stored in a memory of IMD 14, programmer 20 or another device) may indicate that patient 12 is engaging in an activity that may increase the possibility of an occurrence of an involuntary voiding event, and, therefore, an inhibitory physiological response related to voiding (e.g., a reduction in bladder contraction frequency) provided by the first stimulation therapy may be desirable while patient 12 is engaging in the activity.

Instead of or in addition to the activity level of patient 12, IMD 14 can initiate the delivery of the first stimulation therapy to patient 12 upon detecting a posture state associated with a relatively high probability of an occurrence of an involuntary voiding event (compared to other posture states) based on the signal from sensor 22. For example, patient 12 may be more prone to an involuntary voiding event when patient 12 is in an upright posture state compared to a lying down posture state. IMD 14 may, for example, store a plurality of motion sensor signals and associate the signals with particular patient posture states using any suitable technique. IMD 14 may flag some of the posture states as being posture states for which the first electrical stimulation therapy to help prevent the occurrence of an incontinence event is desirable.

In some examples, IMD 14 controls the delivery of the first stimulation therapy based on a time of day, which can be predetermined and based on time of day-parameters stored by IMD 14. The time of day at which IMD 14 initiates the delivery of the first stimulation therapy can be, for example, associated with a time of day at which patient 12 is more active, such electrical stimulation therapy to help prevent an involuntary voiding event may be desirable. As an example, IMD 14 may not deliver electrical stimulation therapy while patient 12 is sleeping (the sleep times can be associated with predetermined times of day in some examples or the sleep can be detected based on one or more patient parameters), and then initiate the delivery of the first stimulation therapy when patient 12 is awake. In other examples, the times of day at which IMD 14 initiates the delivery of the first stimulation therapy may be selected to be at regular or irregular time intervals. In addition, in other examples, the times of day at which IMD 14 initiates the delivery of the first stimulation therapy can be selected to be a time at which the patient's pelvic floor muscles may be more tired, which may increase the possibility of in an occurrence of an involuntary voiding event, such that lower urinary tract dysfunction therapy may be desirable.

Another trigger event for initiating the delivery of the first stimulation therapy can be the expiration of a timer. The timer used to trigger the first stimulation therapy can be based on, for example, the bladder fill cycle of patient 12. In these examples, IMD 14 can restart the timer upon receiving an indication that the bladder fill cycle of patient 12 has been restarted, e.g., restarted by occurrence of a voiding event, which can be voluntary, but, in some cases, involuntary. At the beginning of a bladder fill cycle, the bladder of patient 12 is substantially empty or low, and fills throughout the cycle. The bladder fill cycle restarts upon emptying of the bladder. The duration of the timer may be selected such that IMD 14 delivers the first stimulation therapy when the bladder fill level of patient 12 is approximated to be at a level in which electrical stimulation therapy delivery may be desirable to help reduce the possibility of the occurrence of an involuntary voiding event. For example, the duration of the timer may be about 50% to about 75% of the way through the bladder fill cycle for patient 12, although other durations can be used and can depend upon the severity of the patient's lower urinary tract dysfunction.

The bladder fill cycle that is used to select the timer duration can be specific to patient 12 or based on a plurality of patients, e.g., with similar lower urinary tract dysfunction disorders. In some examples, the duration of the timer is selected based on the mean, median, or shortest bladder fill cycle duration of patient 12 during a certain period of time (e.g., on the order of hours, days, or weeks), which can be prior to any delivery of stimulation to patient 12, or a time period immediately preceding the time at which the timer duration is selected.

In some examples, instead of or in addition to a trigger event detected based on input from sensor 22 or expiration of a timer, the trigger event can include patient input. Thus, IMD 14 may deliver the first stimulation therapy in response to receiving patient input. For example, patient 12 can interact with programmer 20 to provide input that causes IMD 14 to initiate the delivery of the first stimulation therapy. In this way, patient 12 may control delivery of the first stimulation therapy. Patient 12 may initiate the delivery of the first stimulation therapy for any suitable reason. In some cases, patient 12 may be afflicted with urgency or urge incontinence, and upon perceiving an urge to void, patient 12 may provide input that causes IMD 14 to deliver the first stimulation therapy. In this way, therapy system 10 may provide patient 12 with direct control of the lower urinary tract dysfunction therapy.

As discussed above, the first electrical stimulation therapy may have a lower frequency than the second and third electrical stimulation therapies. Compared to a stimulation technique in which the higher frequency second or third electrical stimulation therapies are substantially continuously delivered to patient 12 without regard to the current patient 12 situation, the techniques described herein for selectively delivering the higher frequency second or third electrical stimulation therapies to patient 12 may help reduce neuron habituation or other forms of patient adaptation to stimulation therapy (e.g., the first electrical stimulation therapy) and extend an effective lifetime of the stimulation therapy (e.g., the time for which the stimulation therapy is efficacious eliciting an inhibitory physiological response related to voiding). It has been found that patient 12 may adapt to stimulation delivered by IMD 14 over time, such that a certain level of electrical stimulation provided to a tissue site in patient 12 may be less effective over time. This phenomenon may be referred to as "adaptation." As a result, beneficial effects to patient 12 from the electrical stimulation may decrease over time. While the electrical stimulation levels (e.g., amplitude of the electrical stimulation signal) may be increased to overcome such adaptation, the increase in stimulation levels may consume more power, and may eventually reach undesirable levels of stimulation.

Periodically modifying the frequency of electrical stimulation delivered to patient 12, e.g., to selectively elicit different physiological responses from patient 12, may also help reduce adaptation to the electrical stimulation therapy. For example, rather than delivering stimulation that addresses both lower urinary tract dysfunction and sexual dysfunction of patient 12 without regard to the current patient situation, system 10 is configured to selectively deliver a first electrical stimulation therapy that modulates one or more neural networks involved in lower urinary tract function of patient 12, a second stimulation therapy that modulates one or more neural networks that affect the sexual reflex response of patient 12, and a third electrical stimulation therapy that modulates both neural networks involved in lower urinary tract function of patient 12 and neural networks that affect the sexual reflex response of patient 12.

As an example, if IMD 14 is delivering the first stimulation therapy to patient 12, and IMD 14 receives input from patient 12 (e.g., via programmer 20) that indicates that the second electrical stimulation therapy is desirable, IMD 14 may cease delivering the first stimulation therapy and initiate delivery of the second stimulation therapy in response to the patient input. In this way, the second electrical stimulation therapy is not delivered to patient 12 until a time that patient 12 regards it as desirable. A similar technique may also be used to control delivery of the third electrical stimulation therapy.

Programmer 20 is a device configured to communicate with IMD 14, and can be, for example, a key fob or a wrist watch, handheld computing device, computer workstation, or networked computing device. Programmer 20 includes a user interface that receives input from a user (e.g., patient 12, a patient caretaker or a clinician). In some examples, the user interface includes, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 20 can additionally or alternatively include a peripheral pointing device, such as a mouse, via which a user may interact with the user interface. In some examples, a display of programmer 20 may include a touch screen display, and a user may interact with programmer 20 via the display. It should be noted that the user may also interact with programmer 20 and/or IMD 14 remotely via a networked computing device.

A user, such as a physician, technician, surgeon, electrophysiologist, or other clinician, may also interact with programmer 20 or another separate programmer (not shown), such as a programmer, to communicate with IMD 14. Such a user may interact with a programmer to retrieve physiological or diagnostic information from IMD 14. For example, the user may use programmer 20 to retrieve information from IMD 14 regarding the bladder contraction frequency of patient 12, bladder cycle durations, and/or voiding events. As another example, the user may use a programmer to retrieve information from IMD 14 regarding the performance or integrity of IMD 14 or other components of system 10, such as leads 16, 18, or a power source of IMD 14. In some examples, this information may be presented to the user as an alert if a system condition that may affect the efficacy of therapy is detected.

The user may also interact with programmer 20 to program IMD 14, e.g., select values for the stimulation parameter values with which IMD 14 generates and delivers stimulation and/or the other operational parameters of IMD 14. For example, with the aid of programmer 20, different sets of therapy parameter values (referred to herein as therapy programs) for each of the first, second, and third electrical stimulation therapies may be selected for patient 12, e.g., by testing a plurality of therapy programs on patient 12 and determining which therapy programs elicits the desired physiological responses for the first, second, and third stimulation therapies.

In some examples, patient 12 may interact with programmer 20 to control IMD 14 to deliver the first, second, or third stimulation therapies, to manually abort the delivery of a currently delivered first, second or third stimulation therapy by IMD 14, or to inhibit the delivery of any electrical stimulation therapy by IMD 14, e.g., during voluntary voiding events. When IMD 14 receives the input from programmer 20, IMD 14 may suspend delivery of the first or third stimulation therapies, or all electrical stimulation therapy, for a predetermined period of time, e.g., two minutes, to allow patient 12 to voluntarily void. In some examples, the input from patient 12 that indicates the voluntary voiding may also be used to determine a duration of a bladder fill cycle of patient 12 and control the delivery of the first stimulation therapy in a closed-loop or pseudo-closed-loop manner.

In addition to or instead of interacting with programmer 20 to control therapy delivery, in some examples, patient 12 may interact directly with IMD 14 to control IMD 14 deliver the first, second, or third stimulation therapies, to manually abort the delivery of a currently delivered first, second or third stimulation therapy by IMD 14, or to inhibit the delivery of any electrical stimulation therapy by IMD 14, e.g., during voluntary voiding events. For example, a motion sensor can be integrated into or on a housing of IMD 14, and the motion sensor can generate a signal that is indicative of patient 12 tapping IMD 14 through the skin. The number, rate, or pattern of taps may be associated with the different stimulation therapies, and a processor of IMD 14 may identify the tapping by patient 12 to determine when patient input is received and which of the first, second, or third stimulation therapies is indicated by the patient input.

In some examples, programmer 20 provides a notification to patient 12 that indicates whether the first, second or third stimulation therapy is currently being delivered to patient 12 or notify patient 12 of the prospective delivery of the first, second or third stimulation therapies to provide patient 12 with the opportunity to manually abort the prospective delivery of therapy. In such examples, programmer 20 may display a visible message, emit an audible alert signal or provide a somatosensory alert (e.g., by causing a housing of programmer 20 to vibrate). After generating the notification, programmer 20 may wait for input from patient 12 prior to delivering the stimulation therapy. Patient 12 may enter input that either confirms delivery of indicated first, second or third stimulation therapy, or manually aborts the prospective delivery of the indicated first, second or third stimulation therapy. In the event that no input is received within a particular range of time, programmer 20 may, for example, wirelessly transmit a signal that indicates the absence of patient input to IMD 14. IMD 14 may then elect to deliver or not to deliver the stimulation therapy based on the programming of IMD 14.

IMD 14 and programmer 20 may communicate via wireless communication using any techniques known in the art. Examples of communication techniques may include, for example, low frequency or radiofrequency (RF) telemetry, but other techniques are also contemplated. In some examples, programmer 20 may include a programming head that may be placed proximate to the patient's body near the IMD 14 implant site in order to improve the quality or security of communication between IMD 14 and programmer 20.

System 10 shown in FIG. 1 is merely one example of a therapy system that is configured to selectively deliver the first, second, and third electrical stimulation therapies to selective manage a lower urinary tract dysfunction, sexual reflex response dysfunction of patient 12, or both dysfunctions, respectively. Systems with other configurations of leads, electrodes, and sensors are possible. For example, in other implementations, IMD 14 may be coupled to additional leads or lead segments having one or more electrodes positioned at different locations proximate the spinal cord or in the pelvic region of patient 12. The additional leads may be used for delivering different stimulation therapies to respective stimulation sites within patient 12 or for monitoring at least one physiological parameter of patient 12.

Additionally, in other examples, a system may include more than one IMD. For example, a system may include two IMDs coupled to respective one or more leads. Each IMD can deliver stimulation to a respective lateral side of patient 12 in some examples. In addition, sensor 22 can be external to patient 12 or incorporated into a common housing as IMD 14 in some examples, and multiple sensors can be used to sense a physiological parameter of patient 12.

As another example configuration, a therapy system can include one or more microstimulators instead of or in addition to IMD 14 and leads 16, 18. The microstimulators can have a smaller form factor than IMD 14 and may not be coupled to any separate leads. Rather, the microstimulators can be leadless and configured to generate and deliver electrical stimulation therapy to patient 12 via one or more electrodes on an outer housing of the microstimulators. The microstimulators can be implanted at various locations within the pelvic floor and at different target tissue sites within patient 12, which are selected such that one or more microstimulators can deliver stimulation therapy to target tissue sites on different lateral sides of patient 12 or at different tissue sites to module different neural networks of patient 12. IMD 14 or another microstimulator may act as a "master" module that coordinates the delivery of stimulation to patient 12 via the plurality of microstimulators.

Figure 2:
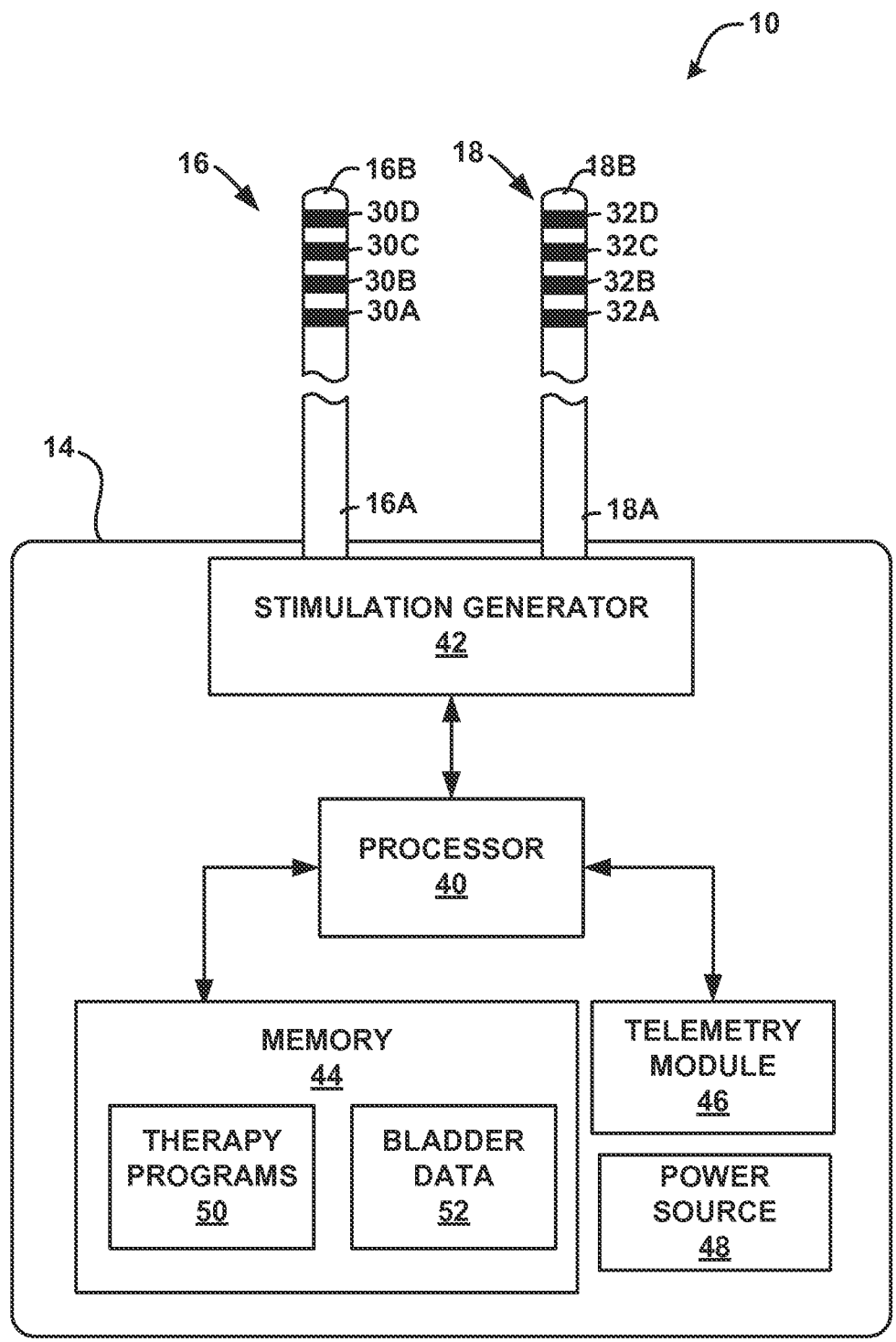
FIG. 2 is a block diagram illustrating an example configuration of an implantable medical device (IMD), which may be a part of the system of FIG. 1.

FIG. 2 is a block diagram illustrating example components of IMD 14. In the example of FIG. 2, IMD 14 includes processor 40, stimulation generator 42, memory 44, telemetry module 46, and power source 48. In other examples, IMD 14 may include a fewer or greater number of components. For example, in some examples, sensor 22 can be a part of IMD 14 and substantially enclosed within the same outer housing as stimulation generator 42 or IMD 14 may include a sensing module electrically connected to leads 16, 18 and configured to sense one or more physiological parameters of patient 12 via electrodes of leads 16, 18.

In the example shown in FIG. 2, leads 16, 18 are electrically coupled to stimulation generator 42, such that stimulation generator 42 may deliver electrical stimulation signals to patient 12 via any subset of electrodes 30A-30D (collectively referred to as "electrodes 30") of lead 16 and electrodes 32A-32D (collectively referred to as "electrodes 32") of lead 18. A proximal end 16A, 18A of each lead 16, 18, respectively, extends from the housing of IMD 14 and a distal end 16B, 18B of each lead 16, 18, respectively, extends to a target therapy site. As discussed above, the target tissue sites for providing therapy to modulate neural networks associated with lower urinary tract dysfunction and sexual reflex response dysfunction can be, for example, proximate a sacral nerve, a pudendal nerve, a dorsal genital nerve, or any combination thereof.

In the example shown in FIG. 2, leads 16, 18 are cylindrical. Electrodes 30, 32 of leads 16, 18, respectively, may be ring electrodes, segmented electrodes, partial ring electrodes or any suitable electrode configuration. Segmented and partial ring electrodes each extend along an arc less than 360 degrees (e.g., 90-120 degrees) around the outer perimeter of the respective lead 16, 18. In some examples, segmented electrodes may be useful for targeting different fibers of the same or different nerves to generate different physiological effects. In other examples, one or more of leads 16, 18 may be, at least in part, paddle-shaped (i.e., a "paddle" lead), and may include an array of electrodes on a common surface, which may or may not be substantially flat.

In some examples, one or more of electrodes 30, 32 may be cuff electrodes that are configured to extend at least partially around a nerve (e.g., extend axially around an outer surface of a nerve). Delivering stimulation via one or more cuff electrodes and/or segmented electrodes may help achieve a more uniform electrical field or activation field distribution relative to the nerve, which may help minimize discomfort to patient 12 that results from the delivery of electrical stimulation therapy. An electrical field may define the volume of tissue that is affected when the electrodes 30, 32 are activated. An activation field represents the neurons that will be activated by the electrical field in the neural tissue proximate to the activated electrodes.

In general, IMD 14 comprises any suitable arrangement of hardware, alone or in combination with software and/or firmware, to perform the techniques attributed to IMD 14 and processor 40, stimulation generator 42, and telemetry module 46 of IMD 14. In various examples, processor 40 can include any one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 may also include a memory 44, which include any volatile or non-volatile media, such as a random access memory (RAM), read only memory (ROM), non-volatile RAM (NVRAM), electrically erasable programmable ROM (EEPROM), flash memory, and the like. Although processor 40, stimulation generator 42, and telemetry module 46 are described as separate modules, in some examples, processor 40, stimulation generator 42, and telemetry module 46 can be functionally integrated. In some examples, processor 40, stimulation generator 42, telemetry module 46 correspond to individual hardware units, such as ASICs, DSPs, FPGAs, or other hardware units.

Memory 44 stores stimulation therapy programs 50 that specify stimulation parameter values for the stimulation therapy provided by IMD 14. In some examples, stimulation therapy programs 50 include one or more stimulation therapy programs for each of the first stimulation therapy, the second stimulation therapy, and the third stimulation therapy. Example stimulation parameter values include a current amplitude of a stimulation signal, a voltage amplitude of the stimulation signal, a frequency of the stimulation signal, a pulse rate of the stimulation signal, a pulse width of the stimulation signal, the duty cycle of the stimulation signal, or the combination and polarity of electrodes 30, 32 with which IMD 14 delivers electrical stimulation to patient 12. The therapy programs associated with the first, second, and third stimulation therapies may differ from each other by at least one stimulation parameter value. For example, the therapy programs associated with the first, second, and third stimulation therapies may have different frequencies, but the same amplitudes.

In some examples, the therapy programs associated with the first electrical stimulation therapy may define an intensity of stimulation that is lower than, substantially equal to, or greater than a threshold stimulation intensity level (also referred to herein as a "threshold intensity" or "threshold intensity level") for patient 12. In addition, in some examples, the therapy programs associated with the second, and third electrical stimulation therapies may define an intensity of stimulation that is substantially equal to or greater than a threshold stimulation intensity level.

The threshold stimulation intensity level may be the stimulation intensity level at which an acute, physiologically significant response (also referred to herein as a threshold physiological response) of patient 12 is first observed when increasing the stimulation intensity from a low intensity to a higher intensity. Stated another way, the threshold stimulation intensity level may be defined as approximately the lowest stimulation intensity level that elicits an acute, physiologically significant response of patient 12. The acute, physiologically significant response may or may not be perceived by patient 12. In some examples, an acute response may be defined as a physiological response that occurs within about 30 seconds (e.g., about 10 seconds) of patient 12 receiving the stimulation.

The desired therapeutic effect is different from the acute physiological response. As one illustration, the desired therapeutic effect of the first and third electrical stimulation therapies may be a reduction in the frequency of bladder contractions in the patient, whereas the acute physiological response may be a motor function caused by the stimulation.

The physiologically significant response used to determine the threshold intensity level can be any suitable physiological response, which may be selected by, e.g., patient 12 or a clinician. The physiological response of interest may be, for example, a patient perception (e.g., the threshold intensity level may be a patient perception threshold), a motor response (e.g., the threshold intensity level may be a motor threshold), a response indicative of capture of a nerve (e.g., the threshold intensity level may be a nerve capture threshold). The nerve capture can be detected using any suitable technique, such as, e.g., sensing afferent or efferent nerve signals via electrodes implanted in patient 12 or external to patient 12 when the stimulation is delivered to patient 12. Other types of physiological responses may be detected and may be unrelated to the type of therapy for which therapy system 10 delivers therapy in some examples. For example, a toe twitch may be considered to be a physiological response that is indicative of a stimulation threshold intensity, but the toe twitch may be a response that does not provide efficacious therapy to patient 12.

In other examples, the physiological response may be related to the type of therapy for which therapy system 10 delivers therapy. For example, the physiological response may be an acute reduction in bladder contraction frequency or intensity. The threshold intensity level, however, may not be the same as a therapy threshold, e.g., a stimulation intensity at which IMD 14 provides efficacious therapy to patient 12 to manage the patient condition (e.g., to reduce bladder contraction frequency).

Whether or not a physiological response is considered to be physiologically significant can be determined by patient 12, a clinician, or another suitable person or device. As an example, the stimulation may elicit movement of a toe of patient 12, and patient 12 may define the movement of the toe as physiologically significant when the movement of the toe is perceptible or when the movement of the toe is above some arbitrary amount defined by patient 12 or the clinician.

Stimulation generator 42 is configured to deliver electrical stimulation to tissue of patient 12 via selected electrodes 30, 32 carried by leads 16, 18, respectively. In some examples, processor 40 controls stimulation generator 42 by selectively accessing and loading at least one of stimulation therapy programs 50 from memory 44 to stimulation generator 42. As discussed below with respect to FIG. 6, patient 12 may select a particular one of stimulation therapy programs 50 from a list using programmer 20 or another suitable device. Processor 40 may receive the selection from programmer 20 (or another suitable device) via telemetry module 46. Stimulation generator 42 can include at least two independently controllable stimulation channels. In other examples, IMD 14 can include one or more independently controllable stimulation channel.

Stimulation generator 42 is configured to generate and deliver electrical stimulation therapy according to stimulation parameter values defined by a therapy program. In this way, the therapy program may define the electrical stimulation therapy delivered to patient 12. In some examples, stimulation generator 42 delivers therapy in the form of electrical pulses. In such examples, relevant stimulation parameters may include a voltage amplitude, a current amplitude, a pulse rate, a pulse width, a duty cycle, or the combination of electrodes 30, 32 with which stimulation generator 42 delivers the stimulation signals to tissue of patient 12. In other examples, stimulation generator 42 delivers electrical stimulation in the form of continuous waveforms. In such examples, relevant stimulation parameters may include a voltage amplitude, a current amplitude, a frequency, a shape of the stimulation signal, a duty cycle of the stimulation signal, or the combination of electrodes 30, 32 with which stimulation generator 42 delivers the stimulation signals to tissue of patient 12.

In some examples, the stimulation parameter values for stimulation programs 50 that define the first electrical stimulation therapy may be selected to relax the patient's bladder, e.g., to reduce a bladder contraction frequency, or otherwise elicit an inhibitory physiological response from patient 12 related to voiding. An example range of stimulation parameter values for the first stimulation therapy that may be effective in treating lower urinary tract dysfunction, e.g., when applied to the dorsal genital nerve, are as follows:

1. Frequency or pulse rate: less than or equal to about 18 Hz, such as between about 0.1 Hz and about 18 Hz, or about 0.1 Hz to about 15 Hz, or about 14 Hz.
2. Amplitude: between about 0.1 volts and about 50 volts, such as between about 0.5 volts and about 20 volts, or between about 1 volt and about 10 volts. For current controlled systems, the amplitude may be between about 0.1 milliamps (mA) and about 50 mA, such as between about 0.5 mA and about 20 mA, or between about 1 mA and about 10 mA.
3. Pulse Width: between about 100 microseconds (µs) and about 400 µs.

In some examples, the stimulation parameter values for stimulation programs 50 that define the second electrical stimulation therapy may be selected to increase the firing of MRF neurons in a brain of patient 12 and change a pudendal motor reflex discharge response. An example range of stimulation parameter values for the second stimulation therapy that may be effective in treating a sexual reflex response dysfunction of patient 12, e.g., when applied to the dorsal genital nerve, are as follows:

1. Frequency or pulse rate: greater than 40 Hz, such as between about 40.1 Hz and about 80 Hz, or between about 40.1 Hz and about 50 Hz.
2. Amplitude: between about 0.1 volts and about 50 volts, such as between about 0.5 volts and about 20 volts, or between about 1 volt and about 10 volts. For current controlled systems, the amplitude may be between about 0.1 mA and about 50 mA, such as between about 0.5 mA and about 20 mA, or between about 1 mA and about 10 mA.
3. Pulse Width: between about 100 µs and about 400 µs.

In some examples, the stimulation parameter values for stimulation programs 50 that define the third electrical stimulation therapy may be selected to relax the patient's bladder or otherwise elicit an inhibitory physiological response related to voiding, e.g., to reduce a bladder contraction frequency, and increase the firing of MRF neurons in a brain of patient 12 and change a pudendal motor reflex discharge response. An example range of stimulation parameter values for the third stimulation therapy that may be effective in treating lower urinary tract dysfunction and treating a sexual reflex response dysfunction of patient 12, e.g., when applied to the dorsal genital nerve, are as follows:

1. Frequency or pulse rate: greater than about 18 Hz and less than or equal to about 40 Hz, such as about 18.1 Hz to 40 Hz.
2. Amplitude: between about 0.1 volts and about 50 volts, such as between about 0.5 volts and about 20 volts, or between about 1 volt and about 10 volts. For current controlled systems, the amplitude may be between about 0.1 mA and about 50 mA, such as between about 0.5 mA and about 20 mA, or between about 1 mA and about 10 mA.
3. Pulse Width: between about 100 µs and about 400 µs.

Additionally, in some examples, the stimulation parameters for one or more of the first, second, and third stimulation therapies may include the parameters that define a therapy cycle, which includes a first time period ("on" periods) during which IMD 14 actively delivers a stimulation signal to patient 12 and a second time period ("off" periods), during which IMD 14 does not deliver any stimulation to patient 12. When stimulation generator 42 delivers the stimulation therapy according to such a therapy cycle, a stimulation signal is not continuously delivered to patient 12, but periodically delivered (e.g., only during the first time period). The first and second time periods may have durations on the order of minutes, but can be longer or shorter depending on the particular patient 12.

As discussed above, in some examples, stimulation generator 42 generates and delivers the first stimulation therapy in an open loop manner, e.g., according to a therapy cycle. In some examples, stimulation generator 42 continues to deliver stimulation therapy to patient 12 according to these stimulation parameters until receiving an instruction from processor 40 to interrupt therapy delivery. In some examples, processor 40 may issue such an instruction to stimulation generator 42 in response to receiving a user input that causes processor 40 to control stimulation generator 42 to generate and deliver the second or third stimulation therapies.

In some examples, memory 44 stores bladder data 52, which can include information related to sensed bladder contractions, bladder impedance and/or posture of patient 12, which may be recorded for long-term storage and retrieval by a user, or used by processor 40 for adjustment of stimulation parameters, such as amplitude, pulse width, and pulse rate. Memory 44 may also store instructions for execution by processor 40, which when executed may cause processor to provide any of the functionality described herein, in addition to stimulation therapy programs 50 and bladder data 52. In some examples, memory 44 includes separate memories for storing instructions, electrical signal information, stimulation therapy programs, and bladder data.

In examples in which stimulation generator 42 delivers the first stimulation therapy to patient 12 in a closed-loop manner, bladder data 52 may store information used by processor 40 to initiate the delivery of the first stimulation therapy. For example, bladder data 52 can include parameters for detecting bladder conditions (e.g., volume or contractions) and trigger events, e.g., patient conditions for which the delivery of the first stimulation therapy is desirable. Example values include, for example, threshold values or baseline values for at least one of bladder impedance, bladder pressure, sacral or pudendal afferent nerve signals, bladder contraction frequency, or external urinary sphincter EMG templates. The threshold values and baseline values may indicate a particular event, such as a bladder contraction or a condition indicative of a voiding-related physiological condition (e.g., a patient state in which there is a relatively high likelihood of an involuntary voiding event). Other example values that processor 40 can use to detect trigger events include a time of day or a timer duration, which, as described above with respect to FIG. 1, can be based on a bladder fill cycle of patient 12.

As described above, in closed-loop stimulation therapy, processor 40 controls stimulation generator 42 to deliver the first stimulation therapy to patient 12 based on at least one feedback, e.g., a signal representative of a physiological response of patient 12 sensed by at least one of sensor 22 or a subset of electrodes 30, 32 of leads 16, 18. For example, processor 40 may control stimulation generator 42 to deliver the first stimulation therapy to patient 12 upon detecting a bladder contraction frequency of patient 12 that is greater than or equal to a threshold bladder contraction frequency or a baseline contraction frequency. In these examples, bladder data 52 may include the threshold bladder contraction frequency or the baseline contraction frequency.

A baseline contraction frequency may be bladder contraction frequency at a time prior to delivery of stimulation therapy by stimulation generator 42. For example, the baseline bladder contraction frequency may be determined by processor 40 after implantation of IMD 14 in patient 12, but before stimulation generator 42 delivers any stimulation therapy to patient 12. In some examples, the baseline bladder contraction frequency may represent the patient state when no therapeutic effects from delivery of stimulation by IMD 14 are present.

In some implementations, processor 40 may, automatically or under control of a user, determine the threshold bladder contraction frequency based on a baseline bladder contraction frequency. For example, the threshold contraction frequency can be a predetermined percentage of the baseline bladder contraction frequency or a percentage of the baseline bladder contraction frequency input by a user via programmer 20. As one example, the threshold frequency may be between approximately 75% and approximately 100% of the baseline bladder contraction frequency.

In other examples, the threshold bladder contraction frequency may not be based on a baseline bladder contraction frequency of patient 12, and may instead be based on clinical data collected from a plurality of patients. For example, the threshold contraction frequency may be determined based on an average bladder contraction frequency of a plurality of patients during a bladder filling time period, e.g., during a time period in which the plurality patients are not experiencing a voluntary or involuntary voiding event. In any case, the threshold contraction frequency may be stored in bladder data 52, and, in some examples, processor 40 may utilize the threshold contraction frequency when delivering stimulation therapy in a closed-loop manner to patient 12.

In other examples, instead of utilizing a threshold bladder contraction frequency or a baseline bladder contraction frequency, processor 40 may control closed-loop delivery of the first stimulation therapy based on an EMG template, EMG characteristics (e.g., an amplitude or frequency value of an EMG), or bladder pressure value, which can each indicate a bladder state in which delivery of the first stimulation therapy is desirable. For example, processor 40 may compare an EMG to an EMG template stored as bladder data 52 to determine whether the contractions of bladder are indicative of a predetermined characteristic which causes processor 40 to control stimulation generator 42 to initiate delivery of the first stimulation therapy. Thus, bladder data 52 can include an EMG template, EMG characteristics, or threshold bladder pressure value in some examples. The EMG template, EMG characteristics, and bladder pressure values can be determined using any suitable technique. In some cases, processor 40 may generate the EMG template or determine the threshold bladder pressure value based on received signals generated by sensor 22 after implantation of IMD 14, but before stimulation generator 42 delivers any stimulation therapy to patient 12. The stored pressure value, EMG template or EMG characteristics with which processor 40 controls the delivery of the first stimulation therapy can indicate a bladder contraction intensity that is indicative of a patient condition in which the first stimulation therapy is desirable, e.g., to reduce the bladder contraction frequency or otherwise reduce the possibility of an occurrence of an involuntary voiding event.

In some examples, bladder data 52 stores parameters with which processor 40 detects a bladder contraction of patient 12 based on a sensed physiological parameter, which can be sensed via sensor 22 or another sensor (e.g., a sensing module of IMD 14). In some examples, processor 40 monitors impedance of a bladder of patient 12 to detect a bladder contraction. Thus, bladder data 52 can include a threshold impedance value that is indicative of the bladder contraction. Processor 40 may, for example, determine an impedance of the bladder and compare the determined impedance value to a threshold impedance value stored in memory 44 as bladder data 52. When the determined impedance value is less than the threshold impedance value stored in bladder data 52, processor 40 detects a bladder contraction. Processor 40 can determine a bladder contraction frequency by, for example, monitoring impedance of the bladder for a predetermined duration of time to detect bladder contractions, and determining a number of bladder contractions in the predetermined duration of time.

In other examples, sensor 22 may be a pressure sensor and processor 40 may detect bladder contractions based on changes in bladder pressure indicated by the pressure sensor. Thus, in some examples, bladder data 52 includes a pressure value or a pressure change that is indicative of a bladder contraction. Processor 40 may determine a pressure value based on signals received from sensor 22 and compare the determined pressure value to a threshold value stored in bladder data 52 to determine whether the signal is indicative of a bladder contraction. Processor 40 can monitor bladder pressure to detect bladder contractions for a predetermined duration of time, and determine a bladder contraction frequency by determining a number of contractions of bladder in the predetermined time period.

In some cases, sensor 22 may be an EMG sensor, and processor 40 can detect bladder contractions based on an EMG of a muscle that is being monitored. The muscle is selected to be a muscle that is activated (e.g., contracts) when the patient's bladder contracts, and can be, for example, a bladder wall, a detrusor muscle, or a urinary sphincter muscle. Thus, in some examples, bladder data 52 includes an EMG template or a threshold signal characteristic value (e.g., an amplitude value) that is indicative of a bladder contraction. Processor 40 may compare a characteristic of a sensed EMG signal or the signal waveform itself to the threshold signal characteristic value or EMG template stored in bladder data 52 to determine whether the signal is indicative of a contraction of bladder.

In other examples of closed-loop stimulation therapy, processor 40 may control stimulation generator 42 to initiate the delivery of the first electrical stimulation therapy when processor 40 determines a volume of a bladder of patient 12 is greater than or equal to a threshold bladder volume. As a volume of the patient's bladder increases, so may the possibility of an involuntary voiding event, such that at the threshold bladder volume, delivery of the first stimulation therapy may be desirable to help prevent an involuntary voiding event. A bladder volume can be determined based on, for example, an impedance of a pathway through the bladder.

In addition to instead of the parameters discussed above for controlling closed-loop control of the first electrical stimulation therapy and detecting a bladder contraction frequency processor 40 may control stimulation generator 42 to initiate the delivery of the first electrical stimulation therapy when processor 40 detects a particular activity (e.g., a gross activity level activity level of a limb or torso of patient 12) or posture state of patient 12. In this example, bladder data 52 can include the output of sensor 22 (or another sensor) that is indicative of a patient activity level or patient posture state associated with an increased probability of an occurrence of an involuntary voiding event. Memory 44 may associate patient posture states or activity levels with the first stimulation therapy, such that when processor 40 detects a posture state or activity level associated with the first stimulation therapy, processor 40 controls stimulation generator 42 to generate and deliver the first stimulation therapy to patient 12.

Processor 40 can determine an activity level of patient 12 based on a motion sensor that generates a signal that changes as a function of patient activity level using any suitable technique. For example, processor 40 may determine an activity level of patient 12 by sampling the signal from the motion sensor (e.g., sensor 22 in some examples) and determine a number of activity counts during a sample period, where a plurality of activity levels are associated with respective activity counts. In one example, processor 40 compares the signal generated by the motion sensor to one or more amplitude thresholds stored within memory 44, and identifies each threshold crossing as an activity count. Processor 40 may determine a patient posture state based on a signal from the motion sensor using any suitable technique. In one example, a posture state may be defined as a three-dimensional space (e.g., a posture cone or toroid), and whenever a posture state parameter value, e.g., a vector from a three-axis accelerometer of the motion sensor resides within a predefined space, processor 40 indicates that patient 12 is in the posture state associated with the predefined space.

In examples in which processor 40 controls the delivery of any of the first, second or third stimulation therapies based on a time of day, bladder data 52 can store the one or more times of day at which processor 40 initiates the delivery of the respective stimulation therapy. Processor 40 can include a clock that tracks the time of day.

In examples in which a timer is used to control the timing of the delivery of the any of the first, second or third stimulation therapies, bladder data 52 can store the duration of the timer. As discussed above with respect to FIG. 1, in some examples, the duration of the timer used to control the timing of the delivery of the first electrical stimulation therapy may be based on the bladder fill cycle of patient 12. In some examples, processor 40 selects the duration of the timer and stores it as bladder data 52, or a clinician can select the duration of the timer and transmit the duration to IMD 14 (e.g., via programmer 20) for storage as bladder data 52.

Any of the trigger events described herein for controlling the timing of the delivery of the first, second or third stimulation therapies can be used in any suitable combination to initiate the delivery of the second stimulation therapy.

Closed-loop therapy may allow processor 40 and stimulation generator 42 to deliver more efficacious lower urinary tract dysfunction therapy to patient 12 by timing the delivery of stimulation to respond to a specific physiological state (e.g., a particular bladder contraction frequency or bladder contraction intensity) of patient 12. For example, based on the determined bladder contraction frequency, processor 40 may cause stimulation generator 42 to initiate delivery of the first stimulation therapy to patient 12. In this manner, closed-loop therapy may reduce or substantially eliminate an amount of time that a bladder contraction frequency is at a baseline level (e.g., a level substantially similar to the contraction frequency of bladder prior to delivery of any stimulation therapy).

In some examples, processor 40 controls the delivery of the second and third stimulation therapies, and, in some examples, the first stimulation therapy, based on user input. The user input may be received via programmer 20 and transmitted to IMD 14. For example, as described with respect to FIG. 6, programmer 20 may include a user interface configured to receive user input and when a processor of programmer 20 receives the user input, the processor may transmit a signal to processor 40 of IMD 14 that indicates the user input has been received. The user input may be associated with a respective one of the first, second or third stimulation therapies.

In some examples, the user input may be indicative of a desired (or selected) physiological response from patient 12 to the therapy. For example, patient 12 may provide input via programmer 20 that indicates that an increase in sexual reflex response is desired. In response to receiving such input, processor 40 may control stimulation generator 42 to deliver the second electrical stimulation therapy and, if another electrical stimulation therapy (i.e., the first or third stimulation therapy) is being delivered to patient 12, cease delivery of the other electrical stimulation therapy. As another example, patient 12 may provide input via programmer 20 that indicates both therapy for reducing urgency (e.g., as indicated by the bladder contraction frequency) and increasing the sexual reflex response of patient 12 is desired. In response to receiving such input, processor 40 may control stimulation generator 42 to deliver the third electrical stimulation therapy and, if another electrical stimulation therapy (i.e., the first or second stimulation therapy) is being delivered to patient 12, cease delivery of the other electrical stimulation therapy.

In some examples, the user input may be indicative of a particular therapy program associated with the one of the first, second, or third stimulation therapies. Programmer 20 may, for example, present a user interface that associates each of a plurality of therapy programs stored by programmer 20, IMD 14, or both, with a physiological response elicited by the particular therapy program, and patient 12 may provide input selecting the therapy program. Processor 40 may then select the therapy program indicated by the patient input and control stimulation generator 42 to deliver electrical stimulation therapy according to the selected therapy program, and, if electrical stimulation therapy according to another therapy program is being delivered to patient 12, cease delivery of the other electrical stimulation therapy.

In some examples, stimulation generator 42 delivers the electrical stimulation therapy indicated by the user input (e.g., one or more of the first, second or third electrical stimulation therapies) for a limited, predetermined therapy period, rather than indefinitely. The duration of which may be stored in memory 44 and/or a memory of another device (e.g., programmer 20). The predetermined period of time can be determined by a clinician in some examples and stored in memory 44 of IMD.

In some examples, in addition to or instead of the predetermined therapy period, stimulation generator 42 delivers the electrical stimulation therapy indicated by the user input for a therapy period controlled by patient 12. In such examples, patient 12 may interact with programmer 20 to control the stimulation period during which IMD 14 delivers the stimulation to patient 12. As another an example, processor 40 may control stimulation generator 42 to initiate the delivery of the first, second, or third stimulation therapy indicated by a received input from patient 12 (e.g., by pressing a button on a keypad or touch screen of programmer 20) and control stimulation generator 42 to terminate the delivery of the first, second, or third stimulation therapy upon receiving a second subsequent input from patient 12 indicating the stimulation therapy indicated by the received input should be terminated. Patient input indicating the currently delivered stimulation therapy should be terminated may include, for example, input selecting a different one of the first, second or third stimulation therapies. In operation, processor 40 can receive the patient input via telemetry module 46 and control stimulation generator 42 to deliver therapy according to the received input.

If processor 40 controls the duration of the therapy period of any of the first, second or third stimulation therapies based on both a predetermined period of time and the patient input, processor 40 can, for example, control stimulation generator 42 to deliver the respective stimulation therapy for the longer of the predetermined period of time or the period of time determined based on patient input, or, in other examples, the shorter of those two periods of time.

In other examples, processor 40 controls the duration of the therapy period during which stimulation generator 42 delivers a particular one of the first, second or third stimulation therapies based on a physiological condition of patient 12. For example, in examples in which stimulation generator 42 initiates the delivery of the first stimulation therapy based on a sensed patient condition, stimulation generator 42 may deliver the first stimulation therapy until the condition is no longer detected. As an example, processor 40 can control stimulation generator 42 to initiate the delivery of the first stimulation therapy in response to detecting a bladder impedance less than or equal to a predetermined trigger event threshold and continue delivering the first stimulation therapy until the bladder impedance is greater than the predetermined trigger event threshold. This threshold may be different than that used to detect a bladder contraction. When processor 40 detects a bladder impedance that is greater than the predetermined termination threshold, processor 40 may determine that the volume of the patient's bladder has decreased (e.g., due to voluntary voiding by patient 12), such that termination of the first stimulation therapy is appropriate. In the foregoing example, stimulation generator 42 delivers the first stimulation therapy until a relatively low bladder fill level of patient 12 is detected.

In some examples, processor 40 may control stimulation generator 42 to initiate the delivery of the second or third stimulation therapy based on user input, and then terminate the delivery of the second or third stimulation therapy based on a sensed patient parameter, such as a sensed physiological condition. The sensed patient parameter may be related to sexual activity of patient 12 and can include, for example, a signal from a motion sensor indicative of an activity level of patient 12 or activity type of patient 12 related to sexual activity or the termination of sexual activity. As other examples (used individually or in combination), the sensed patient parameter may be a parameter such as pressure in relevant tissues or structures (e.g., the corpus cavernosum and/or corpus spongiosum), systemic blood pressure, EMG activity of a muscle involved in sexual activity (e.g., the ischiocavernosus or bulbospongiosus muscles), or the like.

Telemetry module 46 includes any suitable hardware, firmware, software or any combination thereof for communicating with another device, such as programmer 20 (FIG. 1). Generally, processor 40 controls telemetry module 46 to exchange information with medical device programmer 20 and/or another device external to IMD 14. Under the control of processor 40, telemetry module 46 may receive downlink telemetry, e.g., patient input, from and send uplink telemetry, e.g., an alert, to programmer 20 with the aid of an antenna, which may be internal and/or external. Processor 40 may provide the data to be uplinked to programmer 20 and the control signals for the telemetry circuitry within telemetry module 46, and receive data from telemetry module 46. Processor 40 may transmit operational information and receive stimulation programs or stimulation parameter adjustments via telemetry module 46. Also, in some examples, IMD 14 may communicate with other implanted devices, such as stimulators, control devices, or sensors, via telemetry module 46.

Processor 40 monitors patient input received via telemetry module 46 and takes appropriate action. As previously described, in some examples, telemetry module 46 may receive an indication from programmer 20 that patient 12 provided input indicative of an imminent voiding event or a request for delivery of the first, second, or third stimulation therapies. Upon receiving the patient input via telemetry module 46, processor 40 may control stimulation generator 42 to generate and deliver the user-indicated stimulation therapy indicated by the patient input for a predetermined amount of time, until a particular patient condition is detected, until a user input is received, or any combination thereof.

Telemetry module 46 can also receive patient input indicating a voluntary voiding event. In response to receiving the input, if the first or third stimulation therapies are being delivered to patient 12, processor 40 may suspend delivery of the first stimulation therapy or the third stimulation therapy for a pre-determined period of time, e.g., 2 minutes. During this time period, processor 40 may ignore signals indicative of the patient parameter, such as signals generated by sensor 22.

Power source 60 delivers operating power to the components of IMD 14. Power source 60 may include a battery and a power generation circuit to produce the operating power. In some examples, the battery may be rechargeable to allow extended operation.

Figure 3:
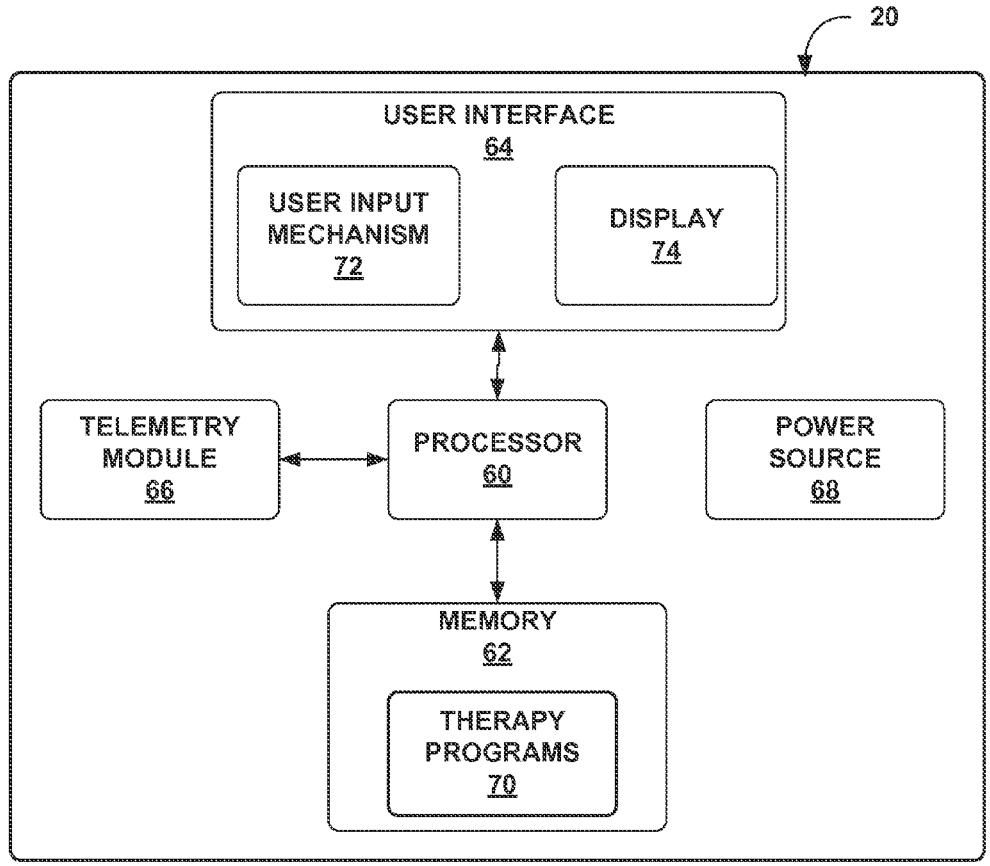
FIG. 3 is a block diagram illustrating an example configuration of an external programmer of the system of FIG. 1.

FIG. 3 is a block diagram illustrating example components of external medical device programmer 20. While programmer 20 may generally be described as a hand-held computing device, the programmer may be a notebook computer, a tablet computer, a cell phone, or a workstation, for example. As illustrated in FIG. 3, programmer 20 may include a processor 60, memory 62, user interface 64, telemetry module 66, and power source 68. Memory 62 may store program instructions that, when executed by processor 60, cause processor 60 and external programmer 20 to provide the functionality ascribed to external programmer throughout this disclosure.

In general, programmer 20 comprises any suitable arrangement of hardware, alone or in combination with software and/or firmware, to perform the techniques attributed to programmer 20, and processor 60, user interface 64, and telemetry module 66 of programmer 20. In various examples, programmer 20 may include one or more processors, such as one or more microprocessors, DSPs, ASICs, FPGAs, or any other equivalent integrated or discrete logic circuitry, as well as any combinations of such components. Processor 60 is configured to control user interface 64 and telemetry module 66, and store and retrieve information and instructions to and from memory 62. Programmer 20 may be a dedicated hardware device with dedicated software for programming of IMD 14. Alternatively, patient programmer 20 may be an off-the-shelf computing device running an application that enables programmer 20 to program IMD 14.

Programmer 20 also, in various examples, may include a memory 62, such as RAM, ROM, PROM, EPROM, EEPROM, flash memory, a hard disk, a CD-ROM, a floppy disk, a cassette, magnetic media, or optical media comprising executable instructions for causing the one or more processors to perform the actions attributed to them. Moreover, although processor 60 and telemetry module 66 are described as separate modules, in some examples, processor 60 and telemetry module 66 are functionally integrated.

Memory 62 may store program instructions that, when executed by processor 60, cause processor 60 and programmer 20 to provide the functionality ascribed to programmer 20 throughout this disclosure. In some examples, memory 62 may further include therapy information, e.g., therapy programs 70 defining the first, second, and third stimulation therapies, e.g., similar to those programs 50 (FIG. 2) stored in memory 44 of IMD 14. In some examples, memory 62 may also store bladder data similar to bladder data 52 stored by IMD 14. In some examples, the actual settings for the therapy programs, e.g., the stimulation amplitude, pulse rate and pulse width data, are stored within therapy programs 62. In other examples, an indication of each therapy program, e.g., a single value associated with each therapy program, may be stored within therapy programs 62, and the actual parameters may be stored within memory 44 of IMD 14 (FIG. 2). The "indication" for each therapy program or group may include, for example, alphanumeric indications (e.g., Therapy Program Group A, Therapy Program Group B, and so forth). The stimulation programs and/or bladder data stored in memory 62 may be downloaded into memory 44 of IMD 14 or vice versa.

User interface 64 is configured to receive input from a user, such as patient 12 or a patient caretaker. Processor 60 may present and receive information relating to stimulation therapy via user interface 64. In the example shown in FIG. 3, user interface 64 includes user input mechanism 72 and display 74. User input mechanism 70 may include any suitable mechanism for receiving input from patient 12 or another user. Example mechanisms for receiving input may include, for example, an alphanumeric keypad, directional buttons that permit patient 12 to scroll up or down through a data display presented on display 74, select items shown on display 74, push buttons, soft-keys, a receiver configured to receive voice activated commands, other inputs activated by physical interactions, magnetically triggered inputs, contacts defined by a touch screen, or any other suitable user interface. In some examples, buttons of user input mechanism 54 may be reprogrammable. That is, during the course of use of patient programmer 20, the buttons of user input mechanism 54 may be reprogrammed to provide different programming functionalities as the needs of patient 12 changes or if the type of IMD 14 implanted within patient 12 changes.

Display 74 may include a color or monochrome display screen, such as a liquid crystal display (LCD), light emitting diode (LED) display or any other suitable type of display. Programmer 20 may present information related to stimulation therapy provided by IMD 14, as well as other information, such as historical data regarding the patient's condition and past usage of different stimulation therapies. Processor 60 monitors activity from input mechanism 72, and controls display 74 and/or IMD 14 function accordingly. In some examples, display 74 may be a touch screen that enables the user to select options directly from the display. In such cases, user input mechanism 72 may be eliminated, although programmer 20 may include both a touch screen and user input mechanism 72. In some examples, user interface 64 may also include audio circuitry for providing audible instructions or sounds to patient 12 and/or receiving voice commands from patient 12.

Patient 12 may use patient programmer 20 to select therapy programs, select a desired physiological response for therapy delivery, generate new therapy programs or program groups, modify one or more therapy parameter values of a stored therapy program through individual or global adjustments, transmit a new therapy program to a medical device, such as IMD 14 (FIGS. 1 and 2). In this way, patient 12 may interact with programmer 20 to control therapy delivery by IMD 14 and control IMD 14 to selectively delivery a stimulation therapy that will elicit a desired physiological response. For example, patient 12 may control therapy delivery by IMD 14 by interacting with user input mechanism 72 to provide an input that is associated with a particular physiological response, stimulation therapy type (e.g., the first, second, or third stimulation therapy), or therapy program. After patient 12 provides input via user input mechanism 72, processor 60 of programmer 20 may transmit to IMD 14, via telemetry module 66, a signal indicative of the selected therapy program, desired physiological response, or the actual therapy parameter values associated with the patient selected therapy program or physiological response.

Telemetry module 66 supports wireless communication between IMD 14 and programmer 20 under the control of processor 60. Telemetry module 66 may also be configured to communicate with another computing device via wireless communication techniques, or direct communication through a wired connection. Telemetry module 66 may be substantially similar to telemetry module 46 described above. In some examples, telemetry module 66 may include an antenna, which may take on a variety of forms, such as an internal or external antenna. Examples of local wireless communication techniques that may be employed to facilitate communication between programmer 20 and another computing device include RF communication according to the 802.11 or BLUETOOTH® specification sets, infrared communication, e.g., according to the IrDA standard, or other standard or proprietary telemetry protocols. In this manner, other external devices may be capable of communicating with programmer 20 without needing to establish a secure wireless connection.

Power source 68 delivers operating power to the components of programmer 20. Power source 68 may include a battery and a power generation circuit to produce the operating power. In some examples, the battery may be rechargeable to allow extended operation.

IMD 14, programmer 20, or both, may control of the timing of the delivery of the first, second, and third stimulation therapies. If external programmer 20 controls the stimulation, programmer 20 may transmit therapy programs for implementation by processor 40 to IMD 14. In addition, or instead, programmer 20 may transmit a signal to IMD 14 indicating that processor 40 should execute locally stored programs or therapy routines. In such a manner, control over the electrical stimulation may be distributed between IMD 14 and external programmer 20, or may reside in either one alone.

As discussed above, in some examples, patient 12 may control the timing of the second and third stimulation therapies delivered by IMD 14, and, in some examples, the first stimulation therapy, via programmer 20. For example, patient 12 may initiate and/or terminate delivery of the second stimulation therapy by IMD 14 via user interface 64. In this way, patient 12 may use programmer 20 to deliver the second stimulation therapy "on demand," such as when patient 12 wants to prioritize the increase in the sexual reflex response over inhibiting bladder contraction frequency (provided by both the first and third stimulation therapies).

Figure 4:
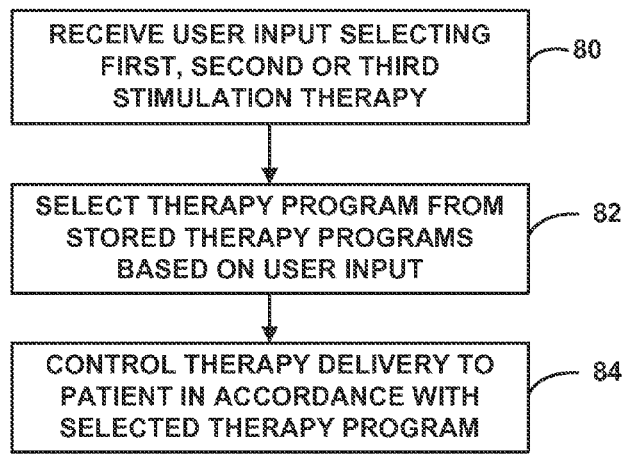
FIG. 4 is a flow diagram of an example technique for delivering stimulation therapy to a patient to selectively and independently address different conditions of a pelvic floor disorder of the patient, such as a lower urinary tract dysfunction and sexual reflex response dysfunction.
Figure 5:
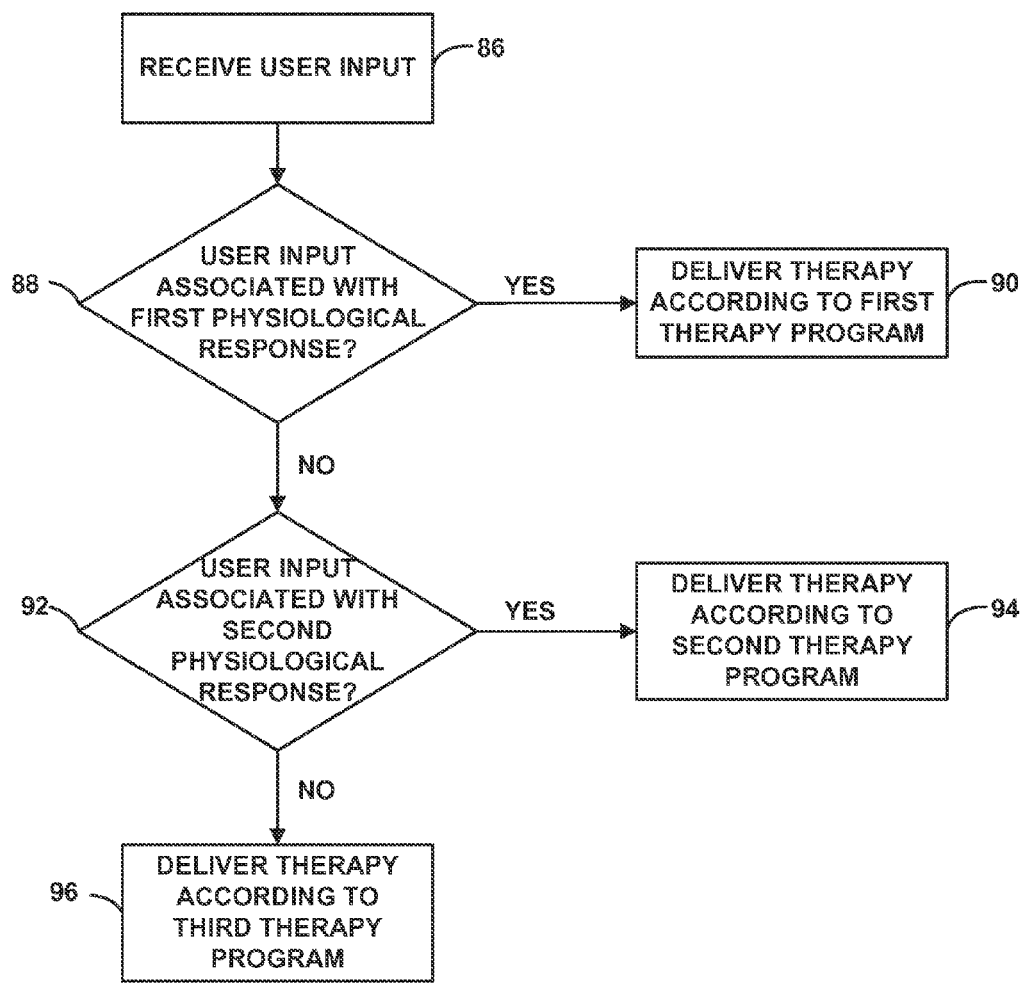
FIG. 5 is a flow diagram of an example technique for selectively delivering one of a first electrical stimulation therapy, a second electrical stimulation therapy, or a third electrical stimulation therapy to a patient in response to patient input.

FIG. 4 is a flow diagram illustrating an example technique implemented by a therapy system, such as therapy system 10 (FIG. 1), to deliver electrical stimulation therapy to patient 12 to selectively and independently address different conditions of a pelvic floor disorder of the patient, such as a lower urinary tract dysfunction and sexual reflex response dysfunction. While FIGS. 4 and 5 are described with respect to therapy system 10, in other examples, the techniques for the first and second stimulation therapies described herein may be implemented by other therapy systems, which may include different components or configurations than therapy system 10. In addition, while processors 40 and 60 are referred to in FIGS. 4 and 5, in other examples, a different combination of devices may perform the techniques shown in FIGS. 4 and 5.

In the technique shown in FIG. 4, processor 40 of IMD 14 receives user input selecting one of the first, second, or third stimulation therapies (80). As discussed above, the user input may be received via user input mechanism 72 of user interface 64 of programmer 20 (FIG. 3), and programmer 20 may transmit the user input to IMD 14 via the respective telemetry modules 66, 46. The user input may be from patient 12. In some examples, the user input may not directly indicate the first stimulation therapy, the second stimulation therapy, or the third stimulation therapy. Rather, in some examples, programmer 20 may present a predetermined list of physiological responses for which the first, second, and third stimulation therapies are configured to elicit, and the user input may select a physiological response from the list.

For example, programmer 20 may associate (in memory 62) the first stimulation therapy with an inhibitory physiological response related to voiding, such as, for example, a reduction in bladder contraction frequency or urgency. Programmer 20 may also associate (in memory 62) the second stimulation therapy with an improved sexual reflex response, and the third stimulation therapy may be associated with both the inhibitory physiological response related to voiding and the improved sexual reflex response. Processor 60 may present a user interface to patient 12 that presents patient with a list of physiological responses and patient 12 may provide input, via user input mechanism 72, selecting a desired physiological response from the list.

In other examples, processor 60 of programmer 20 may present, via display 74, a predetermined list of stimulation types available for patient 12, and the user input may provide input via user input mechanism 72 indicating a desired type of stimulation. For example, the list of therapy types may include "incontinence therapy" (i.e., a name for the first stimulation therapy), "sexual reflex therapy" (i.e., a name for the second stimulation therapy), and "mixed incontinence and sexual reflex therapy" (i.e., a name for the third stimulation therapy). Processor 60 of programmer 20 may also present more discreet labels for the different therapies that are available, such as "Therapy A" (associated with the first stimulation therapy), "Therapy B" (associated with the second stimulation therapy), and "Therapy C" (associated with the third stimulation therapy).

Memory 62 of programmer 20 or memory 44 of IMD 14 may store information associating a particular physiological response, stimulation type or other indicator of a selected therapy with one of the first stimulation therapy, the second stimulation therapy, or the third stimulation therapy, or therapy programs defining each of the first, second, and third stimulation therapies. Accordingly, when processor 40 of IMD 14 or processor 60 of programmer 20 receives user input indicating a physiological response selected by the user from a list of physiological responses or a stimulation type selected from a list of available stimulation types, or another indicator of one of the first, second, or third stimulation therapies, processor 40 or processor 60 may determine the stimulation therapy and the one or more therapy programs associated with the selected stimulation therapy in memory 44 of IMD 14, memory 62 of programmer 20 or a memory of another device (82). Processor 40 may control stimulation generator 42 (FIG. 2) to generate and deliver stimulation to patient 12 in accordance with the stimulation therapy associated with the physiological response (84).

FIG. 5 is a flow diagram of an example technique for selectively delivering one of the first, second or third electrical stimulation therapies to patient 12 in response to patient input. The technique shown in FIG. 5 may be used to provide patient-directed therapy to patient 12. While the technique shown in FIG. 5 primarily refers to processor 60 of programmer 20, in other examples, another processor, such as processor 40 of IMD 14, may perform any part of the technique shown in FIG. 5 alone or in addition to processor 60.

Patient 12 may provide input indicating which of the first, second or third electrical stimulation therapies is appropriate for the current patient situation. In accordance with the technique shown in FIG. 5, processor 60 of programmer 20 receives user input indicating a desired physiological response (86). For example, processor 60 may receive the user input via user input mechanism 72 of user interface 64 (FIG. 3). Patient 12 may interact with user input mechanism 72 by, for example, depressing a button, selecting an input via a touch screen interface, actuating a switch, providing a voice command that is received by a receiver of user input mechanism 72, or by any other suitable mechanism. In other examples, processor 40 of IMD 14 may receive input from patient 12 without the aid of programmer 20. For example, patient 12 may tap the skin near the implant site of IMD 14 in a particular pattern to provide a particular input.

After processor 60 receives the user input (86), processor 60 may determine which of the first, second, or third electrical stimulation therapies the user input is associated with in order to determine which therapy program stimulation generator 42 should use to deliver therapy to patient 12 in response to the user input. In the technique shown in FIG. 5, processor 60 determines whether the user input is associated with a first physiological response elicited by the first electrical stimulation therapy (88). When processor 60 determines the user input is associated with the first physiological response (YES branch of block 88), processor 60 may control IMD 14 to deliver therapy according to a first therapy program that is configured to elicit the first physiological response from patient 12 (90). The first therapy program may be configured in such a manner based on the therapy parameter values of the first therapy program. The therapy parameter values of the first therapy program may be selected such that, when IMD 14 delivers stimulation to patient 12 according to the therapy parameter values, the first physiological response is elicited. In some examples, the first therapy program (as well as the second and third therapy program described below) may be configured specifically for patient 12 or may be selected based on trialing on another patient or a group of other patients.

In some cases, a plurality of therapy programs may be configured to elicit the first physiological response from patient 12. In these examples, processor 60 of programmer 20 or processor 40 of IMD 14 may select one of the therapy program from the plurality of therapy programs associated with the first electrical stimulation therapy.

Processor 60 of programmer 20 may receive the input from patient (88) via user input mechanism 72 of user interface 64 and may transmit an indication of the input to processor 40 of IMD 14 via the respective telemetry modules. As discussed above, in some examples, the indication of the patient input may be a signal associated with the selected physiological response, therapy program, or stimulation therapy, in which case, processor 40 may retrieve the appropriate therapy program from memory 44 based on the patient input. In other examples, processor 60 may transmit, to IMD 14, the indication of the patient input by transmitting, to IMD 14, the actual therapy parameter values of the first therapy program. Other techniques for arranging the communication of the patient input to IMD 14 may also be used.

In the technique shown in FIG. 5, when processor 60 determines that the user input is not associated with the first physiological response (NO branch of block 88), processor 60 may determine whether the user input is associated with a second physiological response elicited by the second electrical stimulation therapy (92). When processor 60 determines the user input is associated with the second physiological response (YES branch of block 92), processor 60 may control IMD 14 to deliver therapy according to a second therapy program that is configured to elicit the second physiological response from patient 12 (94). Again, if more than one therapy program is configured to elicit the second physiological response from patient 12, processor 60 of programmer 20 or processor 40 of IMD 14 may select one of the therapy programs from the plurality of therapy programs associated with the second electrical stimulation therapy.

If processor 60 determines that the user input is not associated with the second physiological response (NO branch of block 92), processor 60 may determine the user input is associated with a third physiological response elicited by the third electrical stimulation therapy (96). When processor 60 determines the user input is associated with the third physiological response, processor 60 may control IMD 14 to deliver therapy according to a third therapy program that is configured to elicit the third physiological response from patient 12 (94). Again, if more than one therapy program is configured to elicit the third physiological response from patient 12, processor 60 of programmer 20 or processor 40 of IMD 14 may select one of the therapy programs from the plurality of therapy programs associated with the third electrical stimulation therapy.

Figure 6:
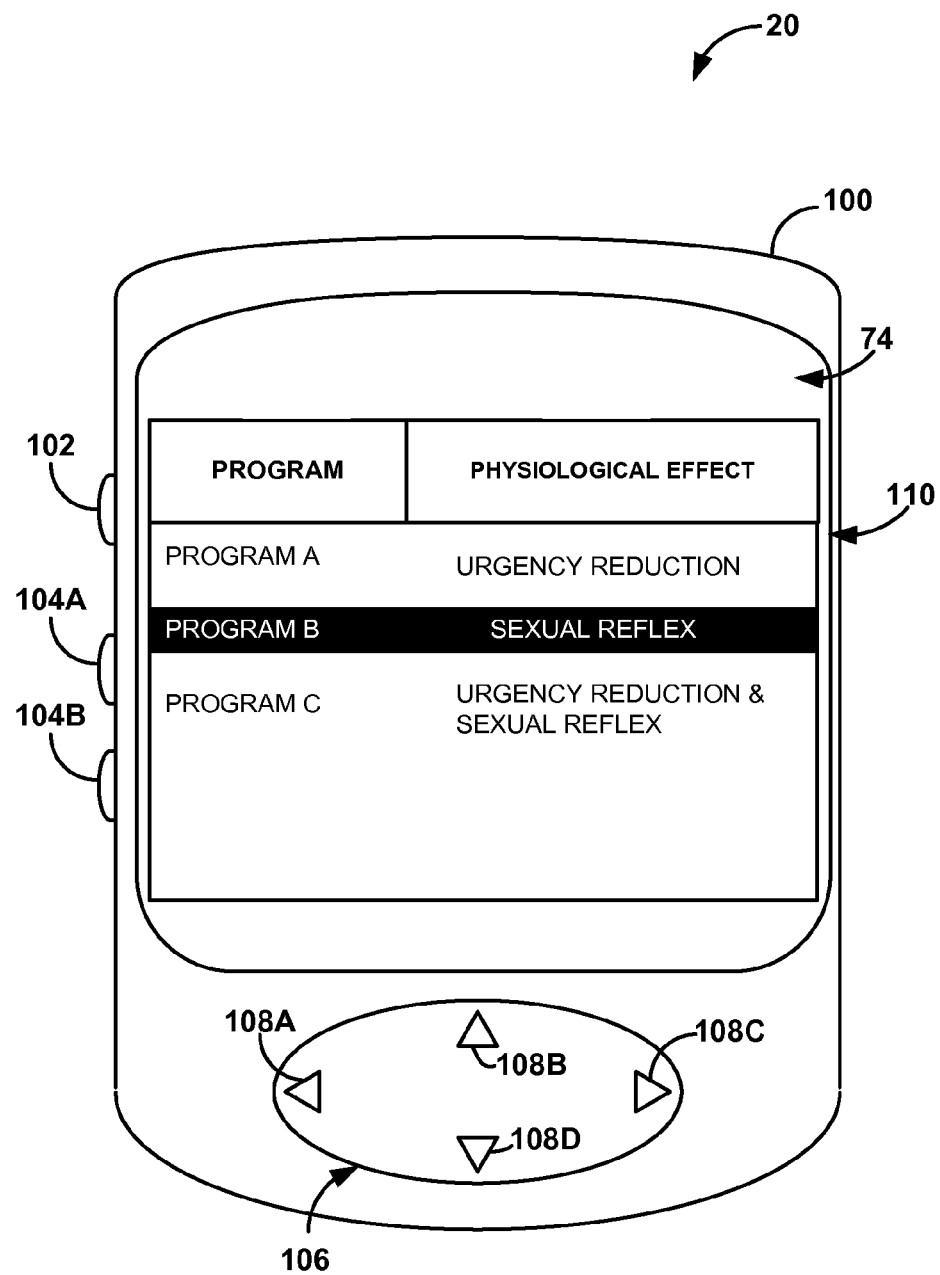
FIGS. 6 and 7 are schematic illustrations of an example medical device programmer that is presenting a graphical user interface with which a patient may interact to provide input to select one of a first electrical stimulation therapy, a second electrical stimulation therapy, or a third electrical stimulation therapy for delivery by a medical device.

FIG. 6 is a schematic illustration of an example programmer 20 with which patient 12 may interact to provide input that selecting one the first, second, or third stimulation therapies. In this way, patient 12 may interact with programmer 20 to control IMD 14 to initiate delivery of a specific type of electrical stimulation therapy, which may depend on the particular physiological response to the electrical stimulation therapy desired by patient 12. Programmer 20 includes display 74, housing 100, power button 102, contrast buttons 104A, 104B, and control pad 106 with directional buttons 108A, 108B, 108C, and 108D. Control pad 106 may be a part of user input mechanism 72 (FIG. 3) of user interface 64 of programmer 20. Housing 100 may substantially enclose the components of programmer 20, such as processor 40 and memory 44. A user may depress power button 102 to turn programmer 20 on or off.

Contrast buttons 104A, 104B may be used to control the contrast of display 74. In addition to displaying a list of therapy programs, physiological responses, stimulation therapy labels, or other indicators for the first, second, and third stimulation therapies, processor 60 of programmer 20 may also present information regarding the type of IMD 14, operational status of IMD 14, patient data, and operational status of programmer 20 on display 74.

In the example shown in FIG. 6, processor 60 of programmer 20 is presenting, via display 74, graphical user interface (GUI) 110 that lists the available electrical stimulation therapies. In particular, in the example shown in FIG. 6, GUI 110 lists example indicators for the first, second, and third stimulation therapies, and provides an interface with which patient 12 may select one of the first, second, or third stimulation therapies. The example indicators for the stimulation therapies provided by GUI 110 include labels for a plurality of therapy programs (i.e., "PROGRAM A," "PROGRAM B," and "PROGRAM C"), where each of the therapy programs corresponds to one of the first, second, or third stimulation therapies. In addition, GUI 110 includes a description of the physiological effect associated with each of the listed therapy programs, such that patient 12 may be able to quickly differentiate between the different therapy programs and select the therapy program that is desired. The physiological effect may correspond to the physiological response of patient 12 to the therapy program.

In some examples, memory 44 of programmer 20 (or another device) may store the information associating a therapy program with a particular physiological effect. The physiological effect of a therapy program may be determined, e.g., based on testing of the electrical stimulation delivered in accordance with the therapy program on patient 12 or a group of patients including or not including patient 12.

In the example shown in FIG. 6, PROGRAM A is a label for the first stimulation therapy, and the physiological effect of PROGRAM A is urgency reduction. In addition, PROGRAM B is a label for the second stimulation therapy, and the physiological effect of PROGRAM B relates to sexual reflex, and PROGRAM C is a label for the third stimulation therapy and the physiological response of PROGRAM B is indicated as being both bladder contraction frequency reduction and sexual reflex.

Although three therapy programs are shown in FIG. 6, in other examples, GUI 110 may present any suitable number of therapy programs, such as therapy programs only associated with the second and third stimulation therapies (e.g., in examples in which IMD 14 delivers the first electrical stimulation therapy to patient 12 in an open loop or based on sensed physiological parameters). In addition, GUI 110 may list more than one therapy program per type of stimulation therapy. For example, GUI 110 may include a plurality of therapy programs associated with the first, second, and third stimulation therapies, and each of the therapy programs may have different therapy parameter values. Patient 12 may find that one therapy program is more efficacious at achieving a particular physiological response than another, even if both therapy programs are associated with the same type of stimulation therapy (one of the first, second, or third stimulation therapies). Thus, providing patient 12 with the option of selecting from a plurality of therapy programs for at least one of the types of stimulation therapy may help increase the odds that an efficacious therapy program is available to patient 12.

In other examples, GUI 110 may present other indicators of the first, second, and third stimulation therapies, such as other types of labels associated with the therapies, therapy programs associated with the therapies, graphical indications of the therapies, or any other indicators that uniquely identify a respective one of the first, second, or third stimulation therapies.

Control pad 106 allows the user to navigate through items presented on display 74. For example, patient 12 may press control pad 106 on any of arrows 108A-108D in order to move between items presented on display 74 or move to another screen not currently shown by display 74. For example, patient 12 may depress or otherwise activate arrows 108A, 108C to navigate between different display screens of the example GUI 110 shown in FIG. 6, and depress or otherwise activate arrows 108B, 108D to scroll through the indicators for the first, second, and third stimulation therapies presented by GUI 110.

Patient 12 may press the center portion of control pad 106 in order to select any highlighted element in GUI 110. For example, patient 12 may scroll to and select "PROGRAM B," which is shown to be highlighted in FIG. 6, in order to provide input selecting PROGRAM B. As discussed above, this input may cause processor 20 to initiate therapy delivery by IMD 14 according to PROGRAM B, provide patient 12 with more information about PROGRAM B, such as the stimulation parameter values defined by PROGRAM B or the stimulation therapy PROGRAM B is associated with (e.g., one of the first, second, or third stimulation therapies), or any other suitable information or combinations of information. In other examples, scroll bars, a touch pad, scroll wheel, individual buttons, a stylus (in combination with a touch screen display 74) or a joystick may perform the complete or partial function of control pad 106.

Figure 7:
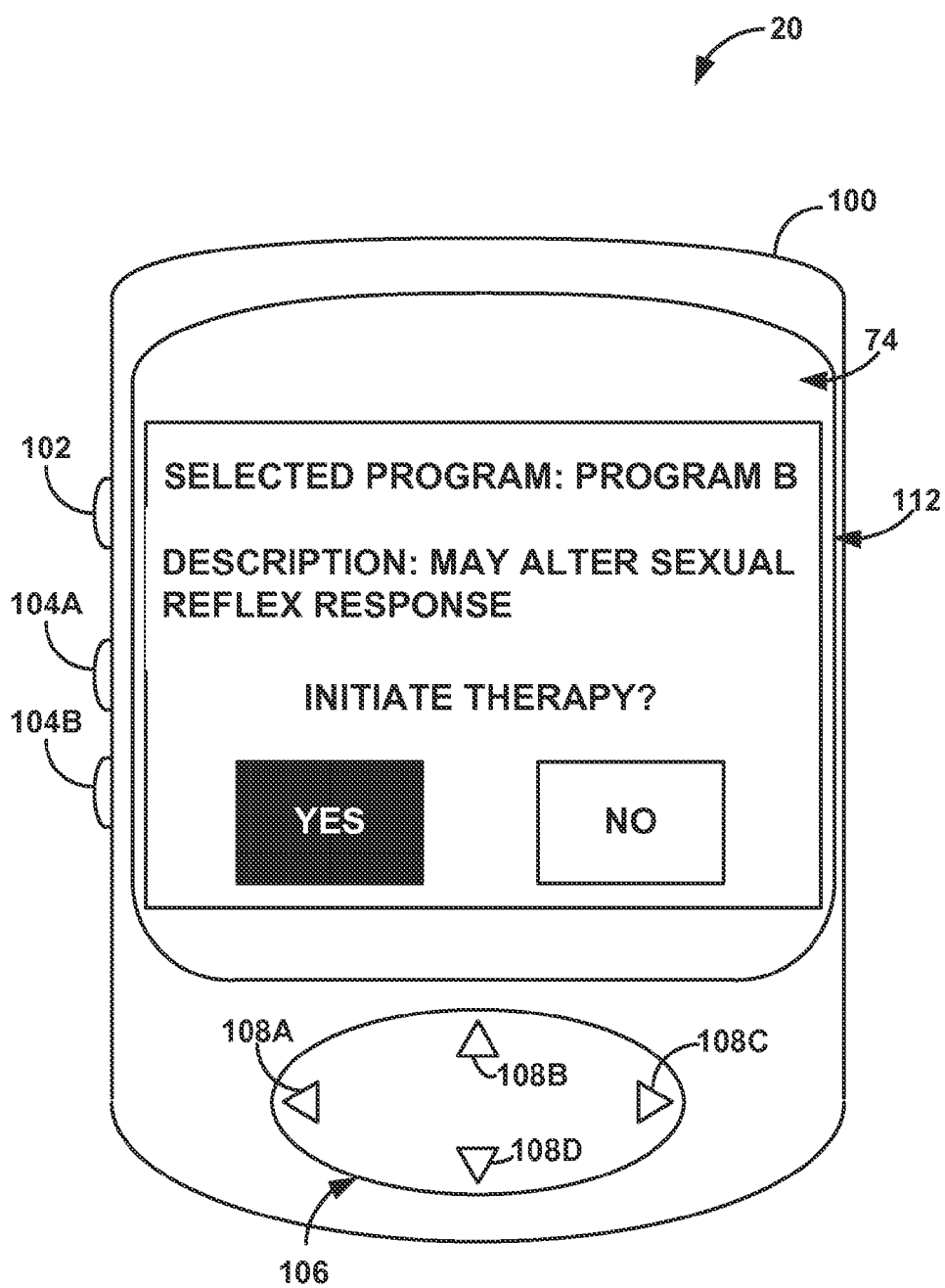

FIG. 7 illustrates an example GUI 112 presented by processor 60 of programmer 20 via display 74 after patient 12 provides input, e.g., using GUI 110, selecting PROGRAM B. Via GUI 112, processor 60 provides confirmation to patient 12 that PROGRAM B was selected. In addition, processor 60 presents, via GUI 112, a description of PROGRAM B that provides additional information with which patient 12 may determine whether PROGRAM B is the appropriate therapy program to select to control therapy delivery. The descriptions of each of the therapy programs may be stored by memory 64 of programmer 20 (or a memory of another device, such as IMF 14) by a clinician, alone or with the aid of patient 12, who may suggest a description that will be understood by patient 12. In the example shown in FIG. 7, the description of PROGRAM B is "may alter sexual reflex response."

GUI 112 also permits patient 12 to provide input that causes IMD 14 to initiate the delivery of electrical stimulation therapy according to PROGRAM B, which corresponds to the second stimulation therapy in which the sexual reflex response of patient 12 is modulated. Patient 12 may, for example, use control pad 106 to scroll to the appropriate box, "YES," which indicates therapy delivery according to PROGRAM B should be initiate, or "NO," which indicates therapy delivery according to PROGRAM be should not be initiated. If patient selects NO, processor 60 may revert to GUI 110, shown in FIG. 6. On the other hand, if patient 12 selects YES, processor 60 may transmit, to IMD 14, a control signal, therapy parameter values, or another signal that causes IMD 14 to initiate therapy delivery to patient 12 according to the second stimulation therapy.

Programmer 20 may present other types of GUIS, and GUIs 110, 112 shown in FIGS. 6 and 7, respectively, are merely examples of GUIs that provide an interface with which patient 12 may provide input selecting one of the first, second, or third stimulation therapies for delivery by patient 12.

Programmer 20 may take other shapes or sizes not described herein. For example, programmer 20 may take the form of a clam-shell shape, similar to cellular phone designs. In any shape, programmer 20 may be capable of performing the functions described herein. Furthermore, in other embodiments, the buttons of programmer 20 may perform different functions than the functions provided in FIGS. 6 and 7. In addition, other embodiments of programmer 20 may include different button layouts or number of buttons. For example, display 74 may be a touch screen that incorporates all user interface and user input mechanism functionality.

Experimental results discussed with respect to FIGS. 8A-17 demonstrate that the dorsal genital nerve may be a target for efficacious electrical stimulation therapy for both lower urinary tract dysfunction and sexual reflex response dysfunction. As discussed below, the experimental results demonstrate that neuromodulation of the dorsal genital nerve of a subject may alter the firing of MRF neurons, which are brainstem neurons known to be involved in sexual arousal, and changed pudendal motor nerve activity, which has been linked to sexual motor behaviors. The experimental results also demonstrate that the frequency of the electrical stimulation delivered to modulate the activity of the dorsal genital nerve may be selected to selectively elicit different physiological responses related to a lower urinary tract dysfunction, a sexual dysfunction, or both. FIGS. 14A-14C illustrate experimental results that indicate that electrical stimulation delivered to the pudendal nerve or L6 spinal nerve may elicit similar responses to those elicited by stimulation delivered to the dorsal genital nerve.

The experimental results discussed with respect to FIGS. 8A-17 demonstrate that electrical stimulation parameters having a frequency of about 14 Hz, a pulse width of about 210 μs, and that define an intensity level that is less than a threshold intensity level of the patient may have a relatively small affect on both the pudendal motor nerve activity linked to sexual motor behaviors and the firing of MRF neurons involved in sexual arousal. In addition, the experimental results demonstrate that electrical stimulation parameters having a higher frequency (relative to 14 Hz) and the same or different amplitudes may cause larger, more selective effects on sexual arousal and sexual reflex response of a subject compared to the electrical stimulation parameters configured to elicit an inhibitory physiological response from the patient related to voiding. The data discussed below with respect to FIGS. 8A-17 demonstrates that electrical stimulation parameter values for affecting lower urinary tract function and sexual reflex function of a subject may both overlap and be dissociable, thereby allowing for the possibility of programming IMD 14 for selective activation of one of the lower urinary tract function or sexual reflex function physiologies at the exclusion of the other, or to configure IMD 14 with electrical stimulation parameter values that are configured to activate both the lower urinary tract function or sexual reflex function physiologies. In this way, different therapy programs can be created to address lower urinary tract dysfunction or sexual function as desired by a patient.

The MRF is a group of brainstem nuclei located in the rostroventral medulla. The MRF neurons are involved in sexual arousal and sexual reflex response; the MRF neurons alter their firing in response to sexual stimuli, including physical stimuli. MRF neurons are believed to be one of the sites that influence spinal motor neuron activity during sexual behavior, and activity of these neurons may be associated with sexual arousal and the sexual reflex response. MRF neurons receive inputs from many pelvic and urogenital structures, including the bladder, urethra, penis and colon.

The pudendal nerve provides motor neurons innervating the perineal and striated sphincter muscles. Activity from the pudendal nerve is involved in both urinary and sexual function reflexes. The pudendal motor reflex discharge is a compound action potential arriving from the motor branch of the pudendal nerve that is associated with spinal motor reflexes associated with sexual function (e.g., erection and ejaculation in males and aspects of orgasm in females). The pudendal motor reflex discharge is one source of efferent discharge during normal sexual function.

It is believed that there is a functional connection between MRF neurons and the pudendal motor reflex discharge. For example, direct electrical stimulation of subsets of the MRF of a subject may depress the dorsal genital nerve-evoked pudendal motor reflex discharge, such that the subject may exhibit a decreased sexual response magnitude to a sexual stimulus and an increased latency to the sexual reflex response. The MRF-evoked depression of pudendal motor reflex discharge activity may be the result of the inhibition of primary sensory afferents rather than a direct effect on motor neuron activity; pelvic nerve evoked pudendal motor reflex discharge may be unaffected by MRF stimulation. Due to the function connection between MRF neurons and the pudendal motor reflex discharge, activity of MRF neurons may be used as an indication of a sexual reflex response of a subject to a sexual stimulus.

Experiments that generated the results discussed below with reference to FIGS. 8A-17 were conducted on adult Wistar rats under urethane anesthesia. Data was analyzed for significance using Student's t-test, repeated measures analysis of variance (ANOVA), and chi-squared tests. A p value of less than about 0.05 was considered significant.

Experiment 1

Experiment 1 was conducted to determine the response of single MRF neurons to dorsal nerve of the penis stimulation in 12 male rats, determine MRF neuron responses to spinal L6/S1 stimulation in 12 male rats, and to determine the response of MRF neurons to dorsal nerve of the clitoris stimulation in 12 female rats. The results of Experiment 1 demonstrate that neuromodulation of the dorsal genital nerve of the rat subjects affects the firing of MRF neurons, such that neuromodulation of the dorsal genital nerve of the rat subjects may alter the sexual reflex response of the rat subjects (based on the known relationship between the MRF neurons and the pudendal motor reflex discharge response discussed above). In addition, the results of Experiment 1 demonstrate that the effects of neuromodulation of the dorsal genital nerve on the MRF neurons show relatively small gender differences.

Offline analysis of the data was performed using software provided by DataWave Technologies of Loveland, Colo., and responses of MRF neurons were determined by subtracting baseline ongoing activity (when present) from the response during neuromodulation or mechanical stimulation. The first frequency and/or amplitude that showed a two-fold increase or decrease in activity from the baseline activity was termed the threshold response. Latency of response was determined from time of stimulation to the onset of the response, and, for bladder responsiveness, the onset of cellular response was compared and classified as 'prior to voiding' or 'at time of void'.

As discussed below, as part of Experiment 1, after isolating individual MRF neurons, responses to the search stimuli were obtained. Neurons responsive to test stimulation were characterized for the response type (excitation or inhibition), response latency, and the frequency and amplitude of the responses. In addition, neuronal response to a variety of electrical stimulation signal amplitudes and frequencies were tested to more fully examine the affect of electrical stimulation on the neuronal responses. Tests to determine the response of MRF neurons to mechanical stimulation (e.g., receptive fields to brush, probing/pressure or pinch of different body areas) were also conducted in order to characterize the relationship between MRF neurons and the sexual reflex response. Finally, in a subset of rats, a catheter and pressure transducer was inserted into the bladder to be able fill the bladder and record intra-bladder pressure.

In Experiment 1, after urethane anesthesia was inducted in the rat subjects, the rats were each placed in a stereotaxic apparatus with hip pins and ear bars. For each subject, after a craniotomy, the cerebellum was removed and tungsten electrodes were lowered with a motorized drive (available from FHC, Inc. of Bowdoinham, Me.) to the MRF of the subject. Stereotaxic coordinates used for recording the activity of the MRF neurons of the subjects were 3200-3400 micrometers (μm) rostral to the obex, 400-800 μm lateral to midline and 2800-3000 μm dorsal-ventral from the brainstem surface of the respective subject. Single-unit, extracellular recordings came from multiple nuclei within the MRF, including the rostral part of the nucleus reticularis gigantocellularis (NRGC), Gi pars alpha (GiA) and lateral paragigantocellularis (LPGi). A search stimulus (i.e., short trains of 50 Hz, amplitude set to five times the pudendal reflex threshold, 100 μs pulses delivered to the dorsal genital nerve) was used to identify responsive MRF neurons. The pudendal reflex threshold was determined to be the amplitude of electrical stimulation at which the first compound action potential was visually observed. In different sub-experiments of Experiment 1, a custom-made platinum bipolar nerve cuff was placed around the L6/S1 spinal nerve trunk, the dorsal genital nerve to test the effects of neuromodulation on MRF neurons.

After isolating individual MRF neurons, responses to the search stimuli were obtained. Electrical stimulation (having a stimulation period of 1-3 seconds) of a single nerve target was delivered to a plurality of subjects using different frequencies (i.e., from 10 Hz to 90 Hz in 10 Hz steps) and amplitudes (up to about 5 times the pudendal motor threshold (i.e., in range of 5 μA to 400 μA, depending on the subject) and a fixed pulse duration (i.e., 100 μs) to characterize threshold amplitude and frequency at which the firings of MRF neurons were observed and the amplitude and frequency at which maximal firings of the MRF neurons were observed for the stimulation parameter values tested. A total of 236 MRF neurons responsive to the electrical stimulation were recorded, with 102 tested with neuromodulation at the dorsal nerve of the penis, 70 neurons were tested with neuromodulation of the L6/S1 spinal nerves, and the remaining 60 were recorded with neuromodulation of the dorsal nerve of the clitoris. Neurons responsive to test stimulation were characterized for the response type (excitation of inhibition), response latency, and frequency and amplitude threshold responses. In addition, neuronal response to a variety of electrical stimulation signal amplitudes and frequencies were tested to more fully examine the affect of electrical stimulation on the neuronal responses.

Certain similarities were observed for the MRF neurons of the subjects, regardless of whether the electrical stimulation was delivered to the dorsal nerve of the clitoris, the dorsal nerve of the penis, or the L6/S1 spinal nerves. Excitatory responses were found in 62% of MRF neurons, and 27% had inhibitory responses to the electrical stimulation, while the remaining 11% had mixed responses. A mixed response may have occurred, for example, if an MRF neuron was unresponsive to neuromodulation of the dorsal nerve of the penis, but exhibited an excitatory response normally seen in response to mechanical stroking of the face. Response latencies indicated that a minority of neurons (23-32%, depending on the stimulation site) responded with relatively short latencies of less than about 20 milliseconds (ms), while the remaining MRF neurons displayed longer latencies (an average of about 170 ms±12 seconds, to about 220 ms±19 ms, depending on the stimulation site). This data demonstrates that there may be some direct inputs to the MRF, but many of the inputs to the MRF are multi-synaptic in nature. For both the dorsal nerve of the penis and the dorsal nerve of the clitoris, no differences were seen in any response characteristics.

FIG. 8A is a graph that illustrates data indicating a typical excitatory response to a plurality of different stimulation signal frequencies (from 10 Hz to 90 Hz). In particular, FIG. 8A is a raw data trace of a typically excitatory response of an MRF neuron to 50 Hz dorsal nerve of the clitoris stimulation. As shown in FIG. 8A, the activity of the MRF neuron increased after the electrical stimulation was applied at time $T_{STIM}$. To generate the data shown in FIG. 8A, the frequency of electrical stimulation signals having an amplitude greater than the threshold amplitude (an average of about 20 microamps (μA)) and a pulse width of about 100 microseconds for the respective subject was varied in 10 Hz increments as the stimulation was delivered to the subjects.

FIG. 8B illustrates a frequency-response profile for an individual MRF neuron of a subject. For this MRF neuron, the frequency threshold (the frequency at which a two-fold increase in activity from the baseline activity was observed) was 20 Hz and the frequency of electrical stimulation that elicited the greatest relative MRF neuron response was different between the different nerve sites. Based on the data shown in FIGS. 8A and 8B, the lowest frequency that elicited the greatest MRF neuron response was determined.

The average frequency of electrical stimulation that elicited the greatest relative MRF neuron response for the dorsal nerve of the penis stimulation target was about 40 Hz. The average frequency of electrical stimulation that elicited the greatest relative MRF neuron response for the L6/S1 spinal nerve stimulation target was about 30 Hz. The average frequency of electrical stimulation that elicited the greatest relative MRF neuron response for the dorsal nerve of the clitoris stimulation target was about 20 Hz. However, the stimulation signal frequency at which a threshold excitatory response of the MRF neuron was observed was approximately the same at all three nerve targets, i.e., 20 Hz.

FIG. 8B shows that the excitatory response of the MRF neuron increased with increasing frequency. In addition, the stimulation signal amplitude at which a threshold response was observed when electrical stimulation was delivered to the target site of each subject (i.e., the dorsal nerve of the penis, the dorsal nerve of the clitoris, or the L6/S1 spinal nerve), the electrical stimulation also having a frequency of about 50 Hz, which was greater than the motor threshold for the subject).

FIGS. 9A-9C shows the response of an MRF neuron of a subject to bilateral dorsal nerve of the penis neuromodulation and illustrates the dependence of the excitatory response of the MRF neuron on intensity of electrical stimulation delivered to the target site, where the intensity was modulated by modulating the amplitude of the electrical stimulation signal delivered to the subject. The spikes in the recordings shown in FIGS. 9A-9C indicate recorded single action potentials from an individual MRF neuron of the subject. The arrows underneath each of the recordings shown in FIGS. 9A-9C indicate the time at which stimulation was applied to the target.

The data shown in FIG. 9A shows that a stimulation amplitude of about 14 µA, which was below the motor threshold for the subject, failed to induce an excitatory response from the MRF neuron.

The data shown in FIG. 9B shows that, for some subjects, stimulation amplitudes at about 18 µA, which was approximately equal to the motor threshold, took multiple applications of electrical stimulation to induce an excitatory response from the MRF neuron. This phenomenon may be referred to as "wind-up." The excitatory response from the MRF neuron is indicated by an action potential firing, which is shown in FIG. 9B as a spike in the recording.

FIG. 9C is a graph that shows that stimulation amplitudes at higher stimulus intensities (and, in particular, at 30 µA in FIG. 9C) resulted in a larger excitatory response from the MRF neuron. In addition, FIG. 9C shows that less wind-up was needed to elicit the excitatory response from the MRF neuron. As shown in FIG. 9C, there appeared to be a longer period of after-discharges of the MRF neuron after the termination of the electrical stimulation.

Figure 10A:
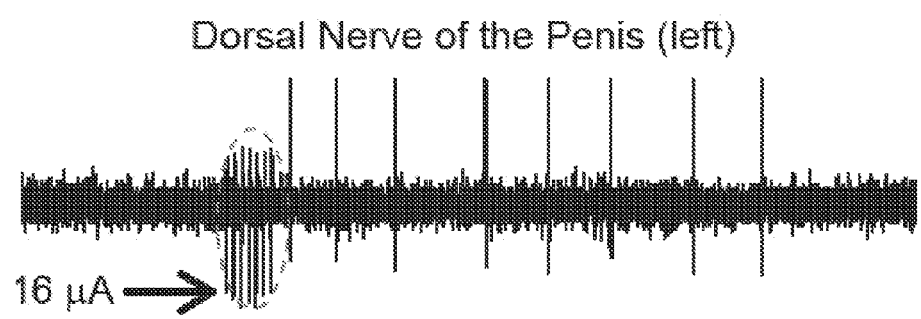
FIGS. 10A and 10B illustrate recordings of a single MRF neuron of a test subject in response to electrical stimulation.
Figure 10B:
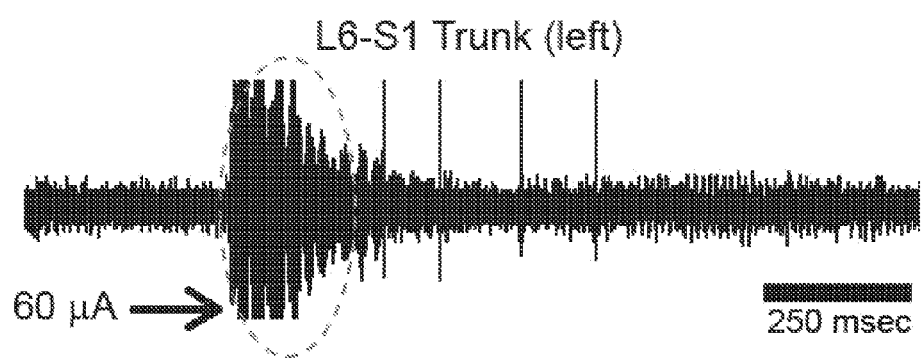

FIGS. 10A and 10B illustrate recordings of a single MRF neuron. In FIG. 10A, the electrical stimulation was delivered to modulate activity of the left dorsal nerve of the penis. In FIG. 10B, the electrical stimulation was delivered to modulate activity of the L6/S1 spinal nerve trunk. The data shown in FIGS. 10A and 10B indicates that the stimulation amplitude threshold for evoking an excitatory response from an MRF neuron may be dependent on the particular nerve site to which the electrical stimulation is delivered.

The dorsal nerve of the clitoris appeared to be the most sensitive to the electrical stimulation, with the MRF cells of the subject having an average amplitude threshold of about 10.5±0.7 µA. The average amplitude threshold for dorsal nerve of the penis neurons was 15.0±0.6 µA. The L6/S1 spinal nerve shows the highest intensity threshold, with an average of 54±4.6 µA needed to induce a MRF cellular response. In these examples, p was less than 0.0001.

In addition to responses to neuromodulation, cells of the subjects were tested for their response to mechanical sexual stimuli. FIGS. 11A-11C are individual recordings of a single MRF neuron of a subject and illustrates responses of the individual MRF neuron to several stimuli. The responses shown in FIGS. 11A-11C were typical for the subjects tested. FIG. 11A illustrates the response of the MRF neuron to a stimuli consisting of electrical stimulation delivered to the dorsal genital nerve of the subject at various amplitudes (7 µA, 8 µA, 9 µA, and 10 µA). FIG. 11B illustrates the response of the MRF neuron to a stimulus consisting of a probe that mimicked a mating stimulus. To mimic the mating stimulus, a glass probe was inserted into the vaginal canal of the female rat subject. FIG. 11C illustrates the response of the MRF neuron to a stimuli consisting of mechanical manipulation of the cervix, which is similar to a sexual stimulus. Of the 51 MRF neurons tested with cervical stimulation, 38 (75%) responded at a mean pressure of about 34±2.7 mmHg.

The responses of the subjects demonstrated in FIGS. 11A-11C indicate that the MRF neurons were responsive to mechanical sexual stimuli, which indicated that the activity of the MRF neurons may indicate the sexual reflex response of the subject to a sexual stimulus.

Experiment 2

Experiment 2 was conducted to characterize the response of single MRF neurons to bladder filling. The same subjects from Experiment 1 were used for Experiment 2. In particular, for MRF neurons tested with dorsal genital nerve neuromodulation in Experiment 1, a total of 100 MRF neurons were also tested for their response to a single cystometry trial (e.g., bladder filling to void). In the absence of electrical stimulation, 55 of these neurons altered firing during the cystometry trial. In the male subjects, MRF neurons tended to alter firing only at the time of voiding. In female subjects, about 43% of the subjects responded before voiding. The remaining neurons responded at the time of void.

In five male rats, 28 trials of cystometry were performed using bilateral dorsal genital nerve neuromodulation in an attempt to directly compare parameters for altering bladder function and MRF neuronal activity. In these experiments, the bladder of the subject was filled until a voiding event. In control trials, the mean pressure at onset of voiding was 25.4±2.7 mm Hg. It was found that for the other trials, the bladder filling/voiding cycle could be prolonged with 90 seconds of bilateral dorsal genital nerve neuromodulation. The average amplitude of the electrical stimulation delivered to modulate the dorsal genital nerve of the each subject was 11.0±0.9 µA, and the frequency at which the bladder filling/voiding cycle was delayed the relatively longest amount of time was 31.4±3.7 Hz. Electrical stimulation having a frequency in a range 10 Hz to about 60 Hz was delivered to the subject in 10 Hz increments to determine the frequency at which the bladder filling/voiding cycle was the longest. The median frequency at which the bladder filling/voiding cycle of the subjects was delayed the relatively longest amount of time was 20 Hz, indicating that in half of the trials, a frequency of less than 20 Hz was the frequency at which voiding was delayed the longest (compared to the other tested frequencies). After the 90 second stimulus, the filling/voiding cycles of the subjects returned to pre-neuromodulation patterns after an average of 2.2±0.4 minutes.

The data from Experiment 2 indicates some separation (at least in male subjects) of the frequencies of electrical stimulation at which bladder effects may be modulated and the frequencies of electrical stimulation at which MRF neuronal activity may be altered. This indicates that, even for the same nerve target, the frequency of electrical stimulation may be modified to selectively modulate lower urinary tract function and sexual function, such that lower urinary tract function therapy and sexual reflex dysfunction therapy may be delivered to a patient in a mutually exclusive manner.

Experiment 3

Experiment 3 was conducted to examine the effects of neuromodulation of the dorsal genital nerve on pudendal motor neuron activity, as well as to examine the ability of stimulation frequency to alter pudendal motor reflex discharge. As discussed above, the pudendal motor reflex discharge of the motor component of the pudendal nerve is involved in the sexual reflex response, and, therefore, the pudendal motor reflex discharge may indicate whether electrical stimulation has altered the sexual reflex response of a subject.

A test stimulation of the right dorsal nerve of the penis was used to observe the effects of neuromodulation on the pudendal motor reflex discharge of male Wistar rat subjects. Thirty-two adult male Wistar rates were used for Experiment 3. In Experiment 3, after inducing anesthesia with urethane, the spinal cord of each subject was transected at the T7-T8 to remove supraspinal influences, e.g., to descending inhibitory controls on sexual function physiology. The motor branch of the compound nerve was manually dissociated from the rest of the nerve, transected, and hooked with a recording electrode. The nerves were exposed and a custom-designed platinum bipolar nerve cuffs were placed around the following nerves: the left dorsal nerve of the penis, the right dorsal nerve of the penis, the left compound pudendal nerve, the left superficial perineal nerve, the left sixth lumbar spinal nerve (L6) and the left first sacral spinal nerve (S1). In addition, the right motor branch of the pudendal nerve was isolated, de-sheathed, and cut distally to record the pudendal motor reflex discharge as a compound action potential (e.g., the electrical activity of the nerve).

The pudendal motor neurons of the rat subjects had little to no ongoing discharge, but began firing during specific motor activities. The test stimulation consisted of electrically stimulating the right dorsal nerve of the penis with a single monophasic pulse having a pulse width of about 100 μs and an amplitude of about three times the motor reflex threshold of the subjects, and recording the resulting pudendal motor reflex discharge. Delivering the monophasic pulse every two seconds resulted in a stable pudendal motor reflex discharge.

To test the effect of neuromodulation of the dorsal genital nerve on the pudendal motor reflex discharge, electrical stimulation at one nerve target was performed, for 20 seconds in a subset of experiments, and 60 seconds, 120 seconds, and 300 seconds periods of stimulation in another subset of experiments. A test stimulation was initially delivered to the subject to first mimic sexual function input and elicit the pudendal motor reflex discharge. Neuromodulation was then delivered to modulate the pudendal motor reflex discharge. The timing of the neuromodulation on the left nerve target was offset with the timing of the test stimulation to evoke the pudendal motor reflex discharge, such that neuromodulation occurred halfway between two test stimulations. The pudendal motor reflex discharge during neuromodulation was compared to the pudendal motor reflex discharge evoked by the test stimulation alone. At each target, electrical stimulation was delivered at multiple frequencies (i.e., 1 Hz, 2 Hz, 5 Hz, 10 Hz, 20 Hz, 25 Hz, 40 Hz, and 50 Hz), multiple pulse widths (100 μs, 300 μs, and 500 μs) and amplitudes (1 and 1.5 times the motor threshold amplitude) in order to determine effective and ineffective stimulation parameter values and target tissue sites for the stimulation.

To analyze the effect of neuromodulation of the dorsal genital nerve on the pudendal motor reflex discharge, three components were examined: 1) the magnitude of the recorded compound action potential, which indicated the pudendal motor reflex discharge response, was quantified as the area under the curve; 2) the latency to the pudendal motor reflex discharge response was measured as the time from the stimulus artifact to the start of the recorded compound action potential; and 3) the duration was defined as the start of the pudendal motor reflex discharge to its return to baseline. In all cases, the response during neuromodulation was divided by the control pudendal motor reflex discharge response and reported as percent of control.

An example compound action potential indicative of a pudendal motor reflex discharge response to electrical stimulation of the right dorsal nerve of the penis of a rat subject is shown in FIG. 12A and an example compound action potential indicative of a control pudendal motor reflex discharge response is shown in FIG. 12B. In FIG. 12A, the "A" refers to the area under the curve that indicates the magnitude of the recorded compound action potential. The "B" refers to the latency to the pudendal motor reflex discharge response from the initiation of the delivery of electrical stimulation to modulate activity of the right dorsal nerve of the penis of the subject. In addition, in FIG. 12A, the "C" refers to the duration of the pudendal motor reflex discharge response.

Figure 13:
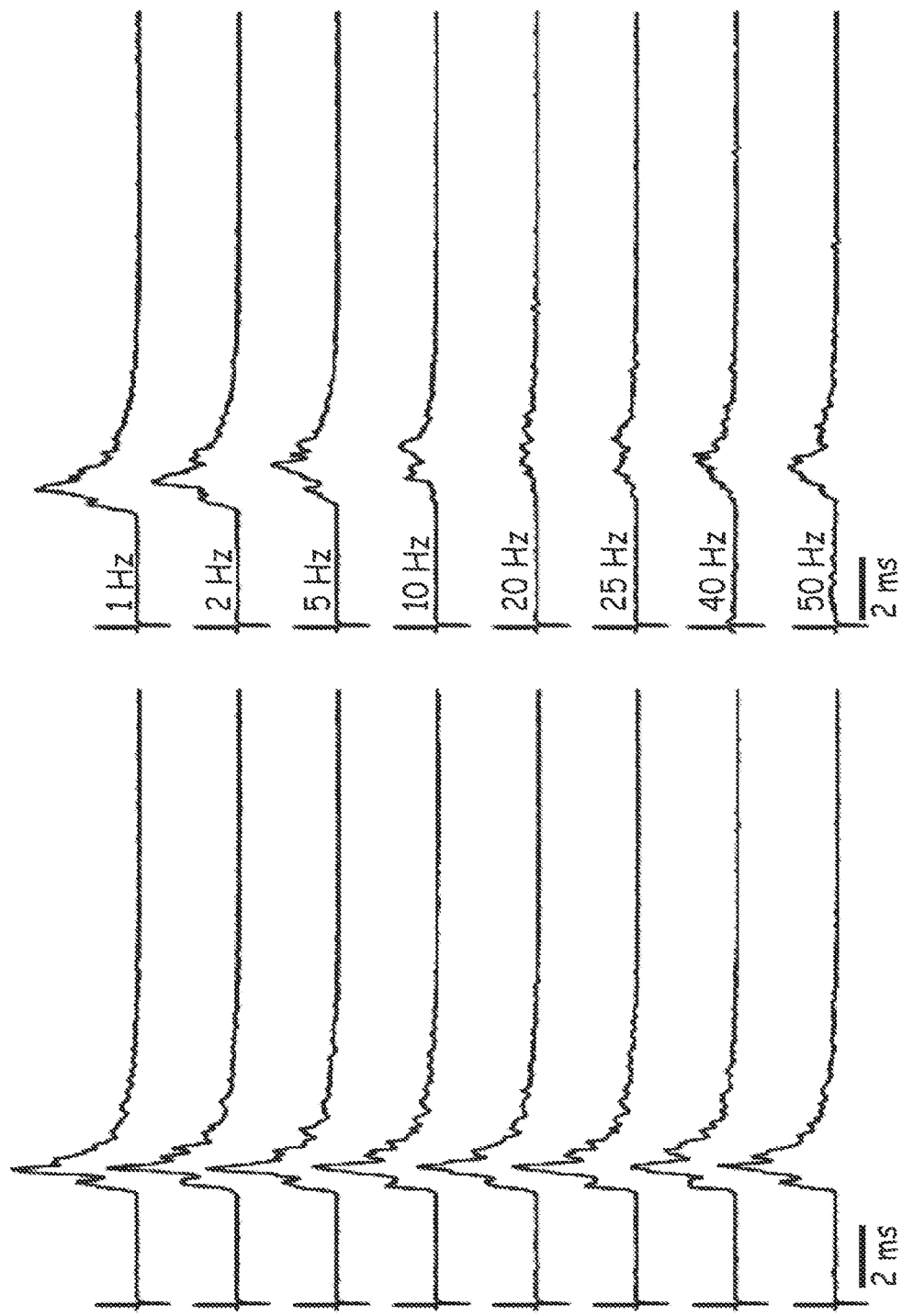
FIG. 13 illustrates the recordings of electrical activity of the motor component of the pudendal nerve of a subject, i.e., the pudendal motor reflex discharge response, in response to different frequencies of electrical stimulation.
Figure 14A:
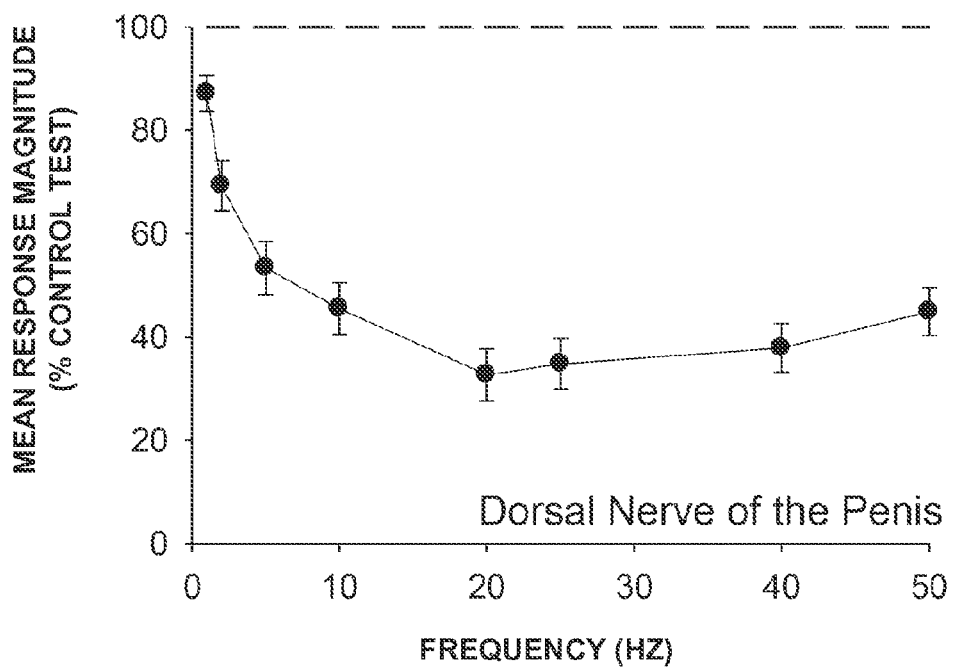
FIGS. 14A-14E are each graphs that illustrates example pudendal motor reflex discharge responses to neuromodulation of various nerve targets in test subjects.
Figure 14B:
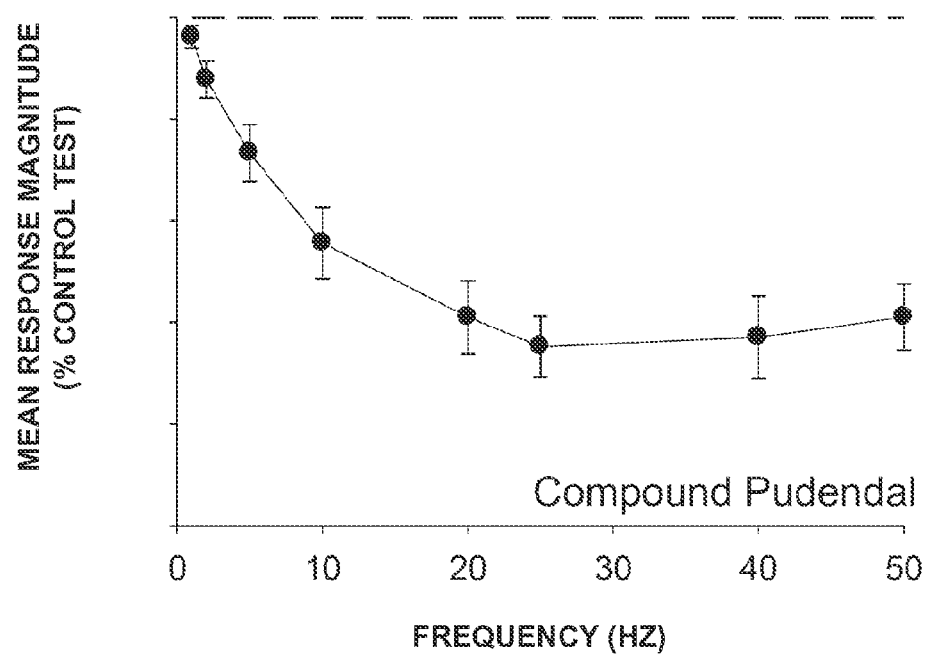
Figure 14C:
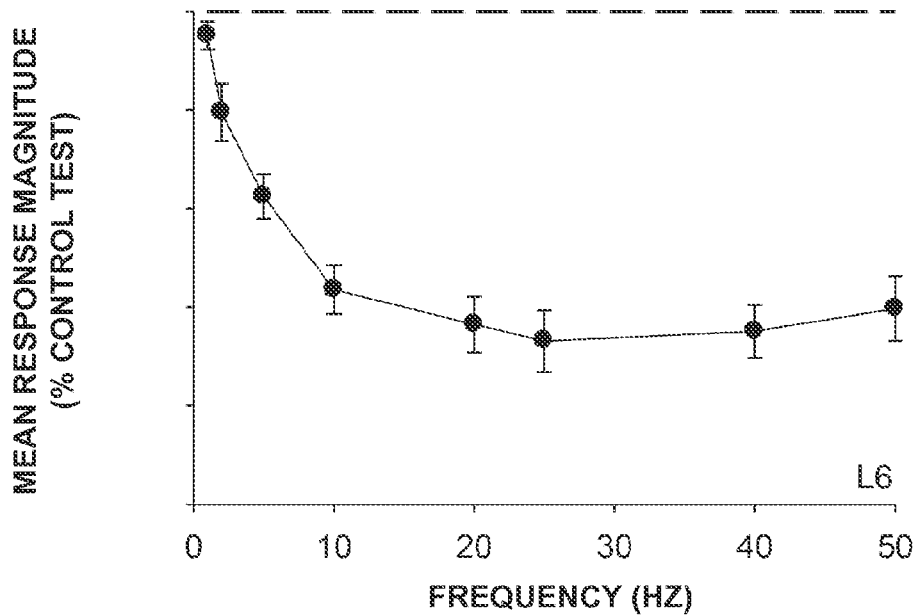
Figure 14D:
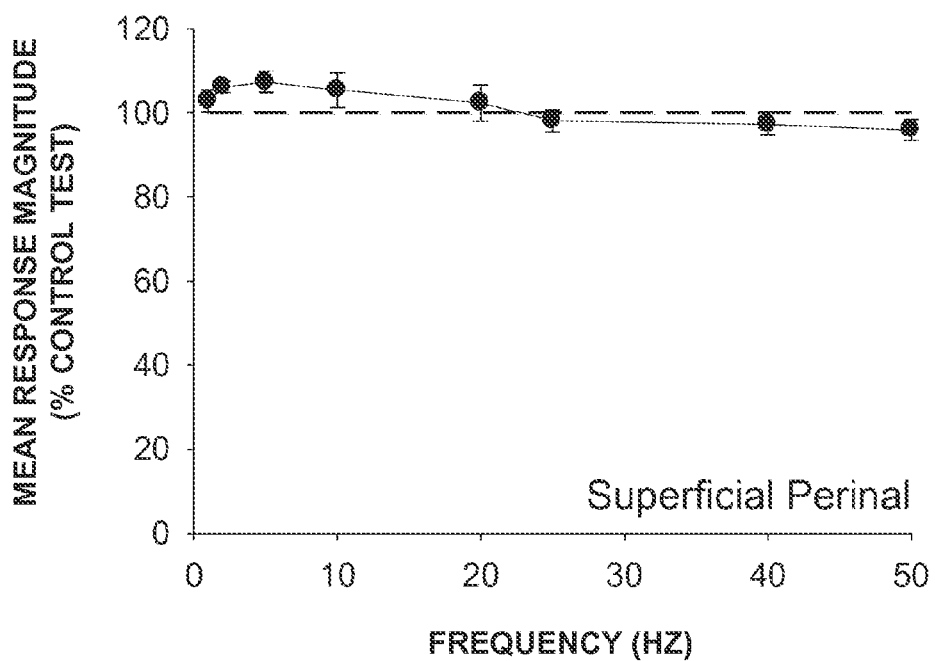
Figure 14E:
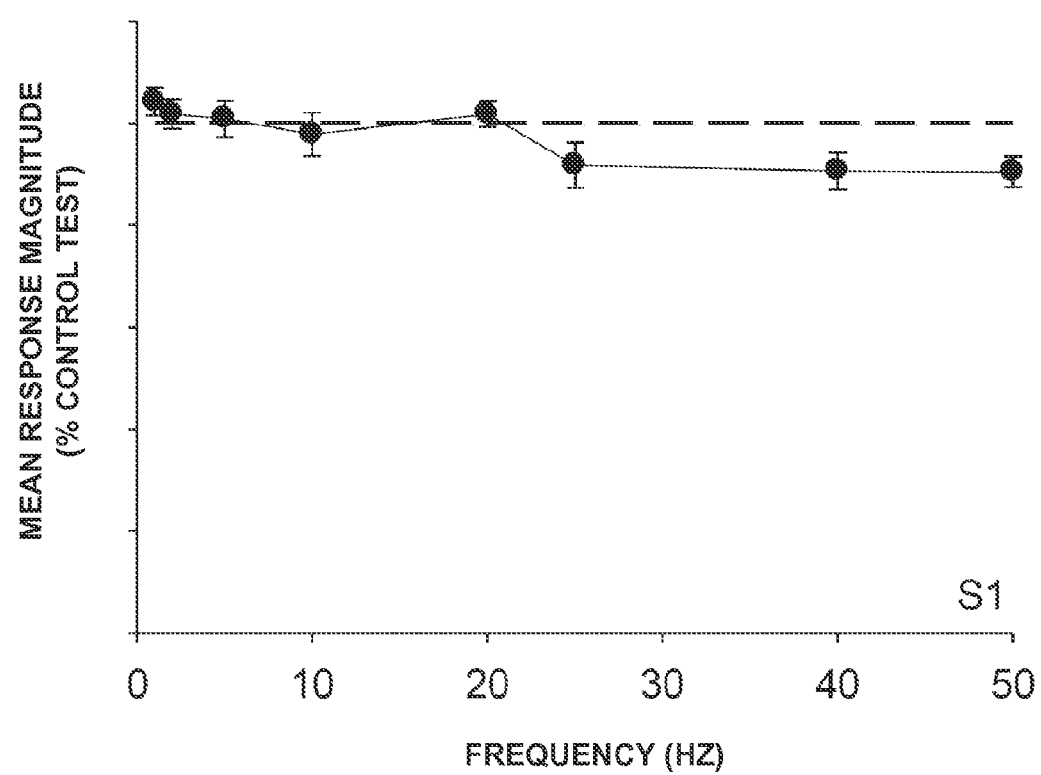

Neuromodulation of the dorsal nerve of the penis evoked stable and repeatable pudendal motor reflex discharge responses from the subjects. For each subject, electrical stimulation having a duration of about 20 seconds, a fixed amplitude (i.e., 1.5 times the motor threshold of the subject) and pulse width (i.e., 100 μs), eight different frequencies (i.e., 1 Hz, 2 Hz, 5 Hz, 10 Hz, 20 Hz, 25 Hz, 40 Hz, and 50 Hz) were delivered to the subjects at five different nerve sites. FIG. 13 illustrates the recordings of electrical activity of the motor component of the pudendal nerve of a subject, i.e., the pudendal motor reflex discharge response, in response to different frequencies of electrical stimulation. The recordings shown in FIG. 13 are representative of the response seen from the subjects in Experiment 3, in which the magnitude of the control pudendal motor reflex discharge (shown on left side of FIG. 13) is reduced in response to certain frequencies of neuromodulation at the opposite dorsal nerve of the penis of the subject. As shown in FIG. 13, the electrical stimulation-induced pudendal motor reflex discharge response decreased in response to electrical stimulation frequencies from 1 Hz to 20 Hz, and for frequencies from 25 Hz to 50 Hz, the pudendal motor reflex discharge response increased, thereby indicating an improvement in the sexual reflex response of the subject.

Averages of the pudendal motor reflex discharge response relative to a control pudendal motor reflex discharge response in response to neuromodulation of various nerve targets in the rat subjects are shown in FIGS. 14A-14E. The graphs shown in FIGS. 14A-14E illustrate the magnitude of the mean response of the recorded compound action potential, which is indicative of the pudendal motor reflex discharge response, to electrical stimulation of various targets at various electrical stimulation frequencies. The mean response is illustrated as a percentage of the control compound action potential (e.g., FIG. 12B). In addition, the control compound action potential is shown as a dotted line in FIGS. 14A-14E.

The data shown in FIGS. 14A-14E indicates that electrical stimulation of the dorsal nerve of the penis (FIG. 14A), compound pudendal nerve (FIG. 14B), and L6 spinal nerve (FIG. 14C) elicited depression of the pudendal motor reflex discharge at frequencies less than or equal to 20 Hz, with a relative maximal inhibition of the pudendal motor reflex discharge occurring at frequencies greater than or equal to 25 Hz. The pudendal motor reflex discharge depression in response to the electrical stimulation of the dorsal nerve of the penis, the compound pudendal nerve, and the L6 spinal nerve indicates a connection between these nerves and the pudendal motor reflex discharge. All three nerve targets showed similar amounts of pudendal motor reflex discharge depression, with the exception that the dorsal nerve of the penis showed larger inhibitory effects at frequencies of less than 10 Hz. Neuromodulation using similar parameters at the superficial perineal nerve (FIG. 14D) and the S1 spinal nerve (FIG. 14E) failed to alter the magnitude of the pudendal motor reflex discharge. The perineal nerve does not contain penile afferents, and the data from neuromodulation of the S1 spinal nerve indicates that little to no afferents from the dorsal nerve of the penis and the pudendal nerve enter the spinal cord at this spinal region in the rat subjects.

Further analysis demonstrated that other components of the pudendal motor reflex discharge, response latency, and response duration, were also altered by neuromodulation, though in a narrower range of frequencies.

Figure 15A:
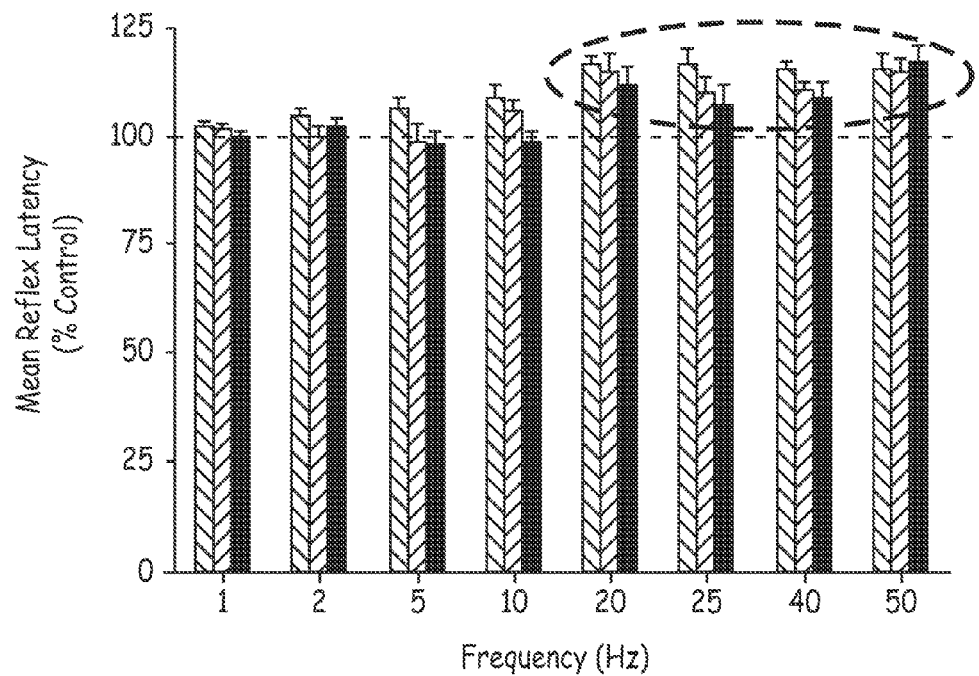
FIGS. 15A and 15B are each bar graphs that illustrates the latency of the pudendal motor reflex discharge of a plurality of test subjects elicited by neuromodulation of the dorsal nerve of the penis, the compound pudendal nerve, and the L6 spinal nerve.
Figure 15B:
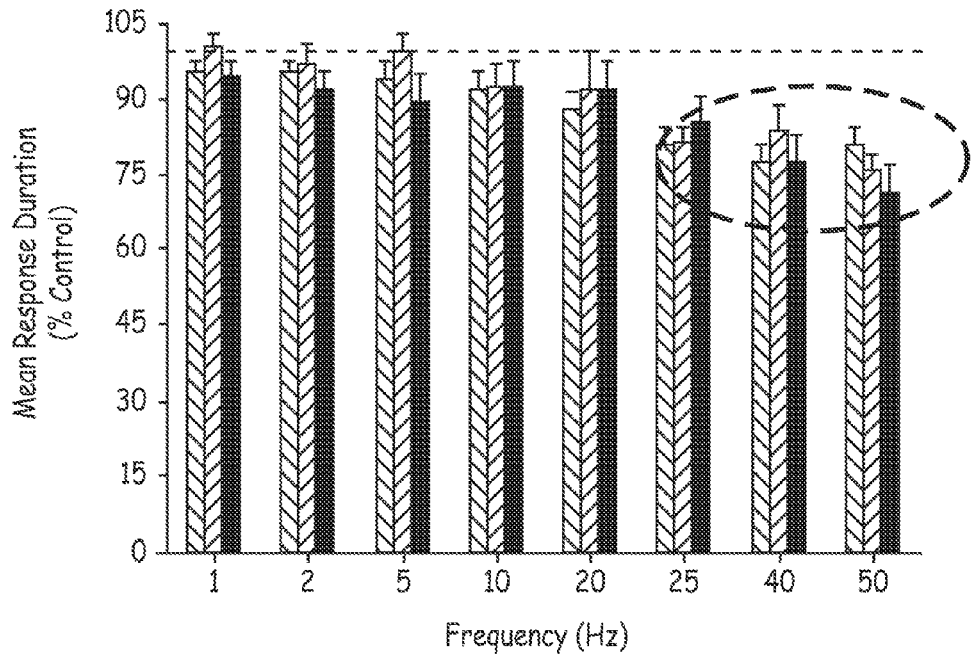

FIGS. 15A and 15B are each a bar graph that illustrates the latency of the pudendal motor reflex discharge of a subject elicited by neuromodulation of the dorsal nerve of the penis (the leftmost bar of the set of three bars associated with each stimulation frequency), the compound pudendal nerve (the middle bar of the set of three bars associated with each stimulation frequency), and the L6 spinal nerve (the rightmost bar of the set of three bars associated with each stimulation frequency) for 9-14 subjects. The y-axis of the bar graphs shown in FIGS. 15A and 15B is the latency of the pudendal motor reflex discharge response as a percentage of the control, which was obtained when no effects of electrical stimulation on the respective nerve were observed. The x-axis of the bar graph shown in FIG. 15A illustrates the frequency of electrical stimulation delivered to the respective nerve. For each subject, the time (in milliseconds) of the onset of the averaged pudendal motor reflex discharge response (reflex latency) was divided by the reflex latency of the test stimulus alone to calculate the percentage of the latency change. The dotted line represents control pudendal motor reflex discharge response.

As shown in FIG. 15A, electrical stimulation having a frequency of 20 Hz to 50 Hz elicited a pudendal motor reflex discharge response having an increased latency relative to the control, whereas frequencies less than 20 Hz did not alter the latency of the response. Similarly, as shown in FIG. 15B, the pudendal motor reflex discharge response duration was also decreased at frequencies between about 25 Hz and 50 Hz. This data shown in FIGS. 15A and 15B demonstrates that some, but not all, nerve targets can inhibit pudendal motor reflex discharge. Furthermore, on at least these test subjects, differential effects were seen on the pudendal motor reflex discharge response, with frequencies above 25 Hz having the largest impact on pudendal motor reflex discharge.

To understand the role of different nerve fiber types on pudendal motor reflex discharge depression, different pulse durations were tested. Shorter pulse widths (e.g., 20 µs and 100 µs) that are believed to only stimulate larger diameter myelinated neurons (Aβ) were compared to a longer pulse width (500 µs) that are believed to only stimulate myelinated (Aβ and Aδ) and unmyelinated (C) fibers were tested.

Figure 16:
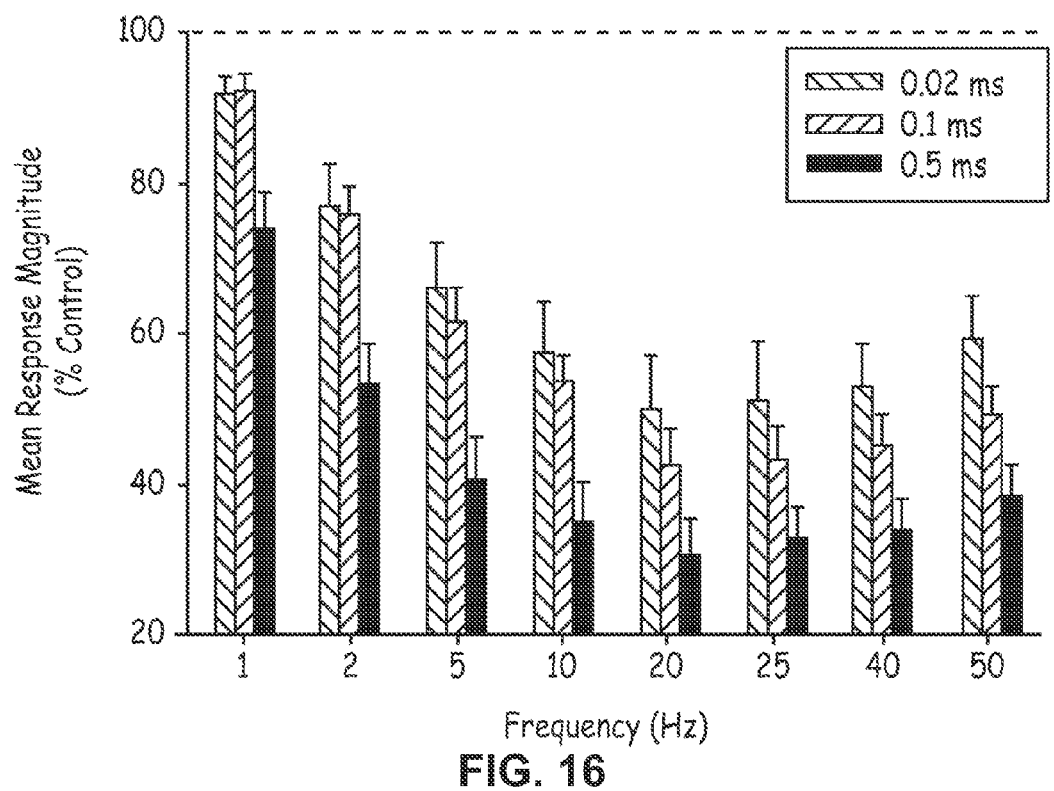
FIG. 16 is a bar graph that illustrates the effect of different pulse widths and frequencies on the depression of the pudendal motor reflex discharge.

FIG. 16 is a bar graph that illustrates the effect of different pulse widths and frequencies on the depression of the pudendal motor reflex discharge. The leftmost bar of the set of three bars associated with each stimulation frequency shows the data from electrical stimulation signals having a pulse width of 0.02 ms, the middle bar of the set of three bars shows the data from electrical stimulation signals having a pulse width of 0.1 ms, and the rightmost bar shows the data from electrical stimulation signals having a pulse width of 0.5 ms. The data shown in FIG. 16 shows that there was significantly less pudendal motor reflex depression using pulse widths less than 500 µs, particularly at lower frequencies (≤10 Hz). Little difference between the three pulse durations on the effects on increased latency and decreased duration (data not shown) were observed. Relatively short pulse widths (e.g., 0.02 ms or 0.1 ms) did not show a difference in pudendal motor reflex discharge depression, while relatively longer pulse widths (e.g., 0.5 ms) had a greater inhibition of pudendal motor reflex discharge at lower frequencies (≤10 Hz). The dotted line in FIG. 16 represents control pudendal motor reflex discharge response for a control group of 10-13 subjects.

The data shown in FIG. 16 indicates that the early component of the effects of electrical stimulation are mediated through larger diameter Aβ fibers and that recruitment of smaller diameter fibers can increase the depression of pudendal motor reflex discharge by activating more afferent fibers. The data shown in FIG. 16 also indicates that effects of neuromodulation may not be specific to a fiber type (e.g. Aβ versus C), but may be attributable to the total number of sensory afferents recruited.

Figure 17:
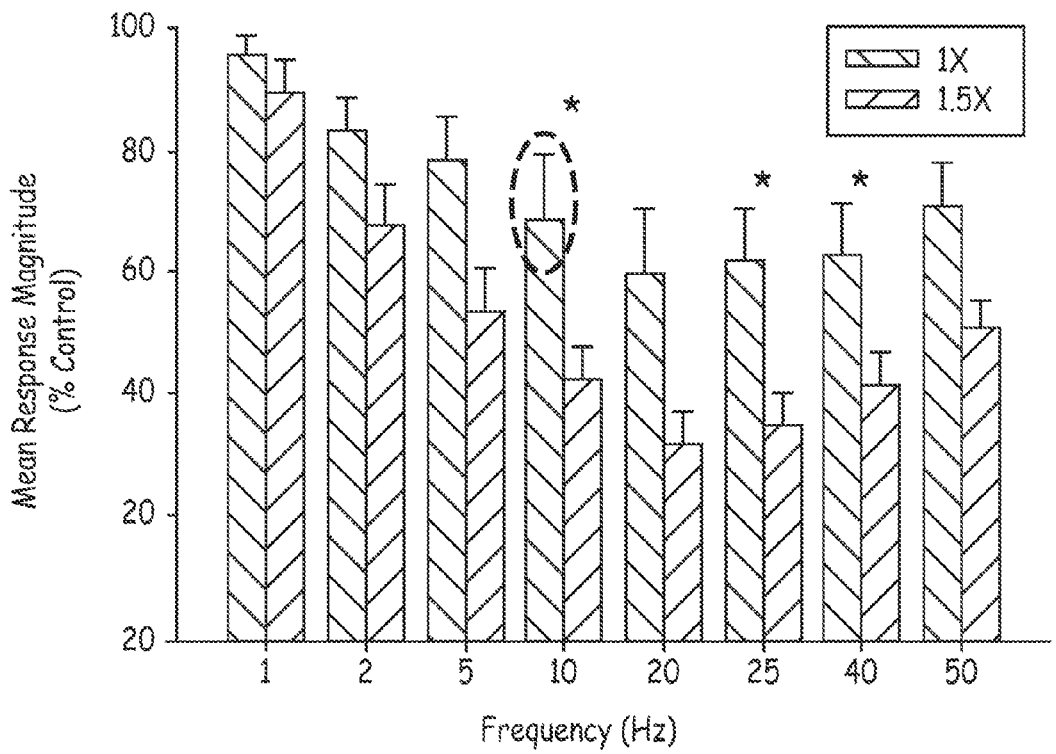
FIG. 17 is a bar graph that illustrates the effects of different frequencies of dorsal nerve of the penis neuromodulation using either the motor threshold amplitude of the respective subject or 1.5 times the motor threshold amplitude.

Additional experiments were conducted on 8 male rat subjects to determine the effect of different stimulation amplitudes on altering pudendal motor reflex discharge. FIG. 17 is a bar graph that illustrates the effects of different frequencies of dorsal nerve of the penis neuromodulation using either the motor threshold amplitude of the respective subject or 1.5 times the motor threshold amplitude. The left side bar of the set of two bars associated with each stimulation frequency shows the data from electrical stimulation signals having the motor threshold amplitude and the right side bar shows the data from electrical stimulation signals having an amplitude of 1.5 times the motor threshold amplitude.

Similar to the pulse width experiments discussed above that demonstrated an increased pudendal motor reflex discharge depression with longer stimulation durations, at an electrical stimulation frequency of greater than 5 Hz, electrical stimulation having an amplitude of 1.5 times the motor threshold amplitude displayed significantly more pudendal motor reflex discharge depression than electrical stimulation having an amplitude of one times the motor threshold amplitude. At the motor threshold amplitude, no frequency was able to depress the pudendal motor reflex discharge by more than 40%. The circled area in FIG. 17 shows the relatively minimal effects of stimulation parameters found to be maximally effective for quieting bladder in the rat.

The results of the experiments discussed above indicate that neuromodulation of the dorsal genital nerve for urinary dysfunction at frequencies less than about 20 Hz may have a relatively small impact on sexual function physiology. For example, less than 15% of MRF neurons responded to electrical stimulation delivered to the dorsal nerve of the clitoris and having a frequency of about 10 Hz. In addition, electrical stimulation delivered to the dorsal nerve of the penis and having a frequency of about 10 Hz caused about 25% depression of the pudendal motor reflex discharge after about five minutes of stimulation (see FIG. 18 data point at 300 s). Moreover, the amplitude needed for both of these effects was above the motor threshold amplitude for the subject. Comparing results from the dorsal genital nerve to other nerve targets (e.g., the L6/S1 spinal nerve and the pudendal and perineal nerve) show relatively similar effects at all effective targets. The experiments discussed above indicate that neuromodulation of the dorsal genital nerve may have an equally low risk for sexual function side effects as neuromodulation of the sacral or pudendal nerve.

The techniques described in this disclosure, including those attributed to IMD 14, programmer 20, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. While the techniques described herein are primarily described as being performed by processor 40 of IMD 14 and/or processor 60 of programmer 14, any one or more parts of the techniques described herein may be implemented by a processor of one of IMD 14, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

What is claimed is:

1. A method comprising:
   with a processor, receiving user input;
   with the processor, selecting, based on the user input, one of a first electrical stimulation therapy configured to elicit an inhibitory physiological response from the patient related to voiding, a second electrical stimulation therapy configured to increase a sexual response of the patient to a sexual stimulus compared to a physiological state of the patient elicited by the first electrical stimulation therapy, or a third electrical stimulation therapy configured to elicit the inhibitory physiological response from the patient related to voiding, and, compared to the physiological state of the patient elicited by the first electrical stimulation therapy, increase the sexual response of the patient to the sexual stimulus; and
   with the processor, controlling a medical device to deliver the selected one of the first electrical stimulation therapy, the second electrical stimulation therapy or the third electrical stimulation therapy to the patient.

2. The method of claim 1, wherein selecting one of the first electrical stimulation therapy, the second electrical stimulation therapy or the third electrical stimulation therapy comprises selecting a therapy program from a plurality of stored therapy programs based on the user input, wherein the plurality of stored therapy programs comprises a first therapy program configured to elicit the inhibitory physiological response from the patient related to voiding, a second therapy program configured to increase the sexual response of the patient to the sexual stimulus compared to the physiological state of the patient elicited by delivery of electrical stimulation in accordance with the first therapy program, and a third therapy program configured to elicit the inhibitory physiological response from the patient related to voiding and increase the sexual response of the patient to the sexual stimulus compared to the physiological state of the patient elicited by delivery of electrical stimulation in accordance with the first therapy program, wherein the first therapy program is configured to elicit a greater inhibitory physiological response from the patient related to voiding than the second therapy program.

3. The method of claim 1, wherein receiving the user input comprises receiving the user input via a medical device programmer.

4. The method of claim 1, wherein receiving the user input comprises receiving the user input via the medical device.

5. The method of claim 1, wherein receiving the user input comprises receiving input indicating a selected physiological response of the patient to electrical stimulation therapy delivered by the medical device, and wherein selecting one of the first electrical stimulation therapy, the second electrical stimulation therapy or the third electrical stimulation therapy comprises:
   determining which of the first electrical stimulation therapy, the second electrical stimulation therapy, and the third electrical stimulation therapy is associated with the selected physiological response; and
   selecting the first electrical stimulation therapy, the second electrical stimulation therapy, or the third electrical stimulation therapy associated with the selected physiological response.

6. The method of claim 1, wherein the first electrical stimulation therapy comprises a frequency less than or equal to about 18 Hertz, the second electrical stimulation therapy comprises a frequency of greater than about 40 Hertz, and the third electrical stimulation therapy comprises a frequency of greater than about 18 Hertz to less than or equal to about 40 Hertz.

7. The method of claim 1, further comprising, prior to receiving the user input, controlling the medical device to deliver the first electrical stimulation therapy to the patient, wherein selecting, based on the user input, one of the first, second, or third electrical stimulation therapies comprises selecting one of the second or third electrical stimulation therapies based on the user input, and wherein controlling the medical device to deliver the selected one of the second or third electrical stimulation therapies comprises:
controlling the medical device to stop delivering the first electrical stimulation therapy to the patient in response to receiving the user input; and, subsequently,
controlling the medical device to deliver the selected one of the second or third electrical stimulation therapies.

8. The method of claim 7, wherein controlling the medical device to deliver the first electrical stimulation therapy to the patient comprises:
receiving a signal from a sensor; and
controlling the medical device to deliver the first electrical stimulation therapy to the patient based on the signal from the sensor.

9. A system comprising:
a medical device; and
a processor configured to receive input from a user, and select, based on the user input, one of a first electrical stimulation therapy configured to elicit an inhibitory physiological response from the patient related to voiding, a second electrical stimulation therapy configured to increase a sexual response of the patient to a sexual stimulus compared to a physiological state of the patient elicited by the first electrical stimulation therapy, or a third electrical stimulation therapy configured to elicit the inhibitory physiological response from the patient related to voiding and, compared to the physiological state of the patient elicited by the first electrical stimulation therapy, increase the sexual response of the patient to the sexual stimulus, wherein the processor is configured to control the medical device to deliver the selected one of the first electrical stimulation therapy, the second electrical stimulation therapy or the third electrical stimulation therapy to the patient.

10. The system of claim 9, further comprising a memory that stores a plurality of therapy programs, wherein the processor is configured to select one of the first electrical stimulation therapy, the second electrical stimulation therapy or the third electrical stimulation therapy by at least selecting a therapy program from the plurality of stored therapy programs based on the user input, the plurality of stored therapy programs comprising a first therapy program configured to elicit the inhibitory physiological response from the patient related to voiding, a second therapy program configured to increase the sexual response of the patient to the sexual stimulus compared to a physiological state of the patient elicited by delivery of electrical stimulation in accordance with the first therapy program, and a third therapy program configured to elicit the inhibitory physiological response from the patient related to voiding and increase the sexual response of the patient to the sexual stimulus compared to the physiological state of the patient elicited by delivery of electrical stimulation in accordance with the first therapy program, wherein the first therapy program is configured to elicit a greater inhibitory physiological response from the patient related to voiding than the second therapy program.

11. The system of claim 9, further comprising a medical device programmer comprising a user input mechanism configured to receive the user input, wherein the processor is configured to receive the user input via the medical device programmer.

12. The system of claim 9, wherein the medical device is configured to receive the user input, and wherein the processor is configured to receive the user input via the medical device.

13. The system of claim 9, wherein the user input comprise comprises indicates a selected physiological response of the patient to electrical stimulation therapy delivered by the medical device, and wherein the processor is configured to select one of the first electrical stimulation therapy, the second electrical stimulation therapy or the third electrical stimulation therapy by at least:
determining which of the first electrical stimulation therapy, the second electrical stimulation therapy, and the third electrical stimulation therapy is associated with the selected physiological response; and
selecting the first electrical stimulation therapy, the second electrical stimulation therapy, or the third electrical stimulation therapy associated with the selected physiological response.

14. The system of claim 9, wherein the first electrical stimulation therapy comprises a frequency less than or equal to about 18 Hertz, the second electrical stimulation therapy comprises a frequency of greater than about 40 Hertz, and the third electrical stimulation therapy comprises a frequency of greater than about 18 Hertz to less than or equal to about 40 Hertz.

15. The system of claim 9, wherein the processor is configured to control the medical device to deliver the first electrical stimulation therapy to the patient prior to receiving the user input, and wherein the processor is configured to select one of the second or third electrical stimulation therapies based on the user input, and control the medical device to deliver the selected one of the second or third electrical stimulation therapies by at least:
controlling the medical device to stop delivering the first electrical stimulation therapy to the patient in response to receiving the user input; and, subsequently,
controlling the medical device to deliver the selected one of the second or third electrical stimulation therapies.

16. The system of claim 15, further comprising a sensor configured to generate a signal indicative of a patient parameter, wherein the processor is configured to receive the signal from the sensor and control the medical device to deliver the first electrical stimulation therapy to the patient based on the signal from the sensor.

17. A system comprising:
means for receiving user input;
means for selecting, based on the user input, one of a first electrical stimulation therapy configured to elicit an inhibitory physiological response from the patient related to voiding, a second electrical stimulation therapy configured to increase a sexual response of the patient to a sexual stimulus compared to a physiological state of the patient elicited by the first electrical stimulation therapy, or a third electrical stimulation therapy configured to elicit the inhibitory physiological response from the patient related to voiding, and, compared to the physiological state of the patient elicited by the first electrical stimulation therapy, increase the sexual response of the patient to the sexual stimulus; and
means for controlling a medical device to deliver the selected one of the first electrical stimulation therapy, the second electrical stimulation therapy or the third electrical stimulation therapy to the patient.

18. The system of claim 17, wherein the first electrical stimulation therapy comprises a frequency less than or equal to about 18 Hertz, the second electrical stimulation therapy comprises a frequency of greater than about 40 Hertz, and the third electrical stimulation therapy comprises a frequency of greater than about 18 Hertz to less than or equal to about 40 Hertz.

19. The system of claim 17, wherein the means for selecting is configured to select one of the second or third electrical stimulation therapies based on the user input, and the means for controlling the medical device is configured to control the medical device to deliver the first electrical stimulation therapy to the patient prior to receiving the user input, control the medical device to stop delivering the first electrical stimulation therapy to the patient in response to receiving the user input; and, subsequently, control the medical device to deliver the selected one of the second or third electrical stimulation therapies.

20. The system of claim 19, further comprising means for generating a signal indicative of a patient parameter, wherein the means for controlling is configured to receive the signal from the sensor and control the medical device to deliver the first electrical stimulation therapy to the patient based on the signal from the sensor.

* * * * *